United States Patent
Burdulis, Jr. et al.

(10) Patent No.: US 7,534,263 B2
(45) Date of Patent: *May 19, 2009

(54) SURGICAL TOOLS FACILITATING INCREASED ACCURACY, SPEED AND SIMPLICITY IN PERFORMING JOINT ARTHROPLASTY

(75) Inventors: Albert G. Burdulis, Jr., San Francisco, CA (US); Wolfgang Fitz, Sherborn, MA (US); Rene Vargas-Voracek, Sunnyvale, CA (US); Philipp Lang, Lexington, MA (US); Daniel Steines, Lexington, MA (US); Konstantinos Tsougarakis, Sunnyvale, CA (US)

(73) Assignee: ConforMIS, Inc., Burlington, MA (US)

( * ) Notice: Subject to any disclaimer, the term of this patent is extended or adjusted under 35 U.S.C. 154(b) by 81 days.

This patent is subject to a terminal disclaimer.

(21) Appl. No.: 11/002,573

(22) Filed: Dec. 2, 2004

(65) Prior Publication Data
US 2005/0234461 A1    Oct. 20, 2005

Related U.S. Application Data

(63) Continuation-in-part of application No. 10/724,010, filed on Nov. 25, 2003, which is a continuation-in-part of application No. 10/305,652, filed on Nov. 27, 2002, which is a continuation-in-part of application No. 10/160,667, filed on May 28, 2002.

(60) Provisional application No. 60/380,695, filed on May 14, 2002, provisional application No. 60/380,692, filed on May 14, 2002, provisional application No. 60/363,527, filed on Mar. 12, 2002, provisional application No. 60/293,488, filed on May 25, 2001.

(51) Int. Cl.
*A61F 2/08*   (2006.01)
*A61B 17/58*  (2006.01)

(52) U.S. Cl. ............................ 623/14.12; 606/88
(58) Field of Classification Search ............ 606/86, 606/87, 88, 89, 82, 80, 96, 98; 623/14.12
See application file for complete search history.

(56) References Cited

U.S. PATENT DOCUMENTS 3,798,679 A    3/1974   Ewald ............................. 3/1

(Continued)

FOREIGN PATENT DOCUMENTS

DE          3516743         11/1986

(Continued)

OTHER PUBLICATIONS

Taha et al., "Modeling and design of a custom made cranium implant for large skull reconstruction before a tumor removal", Phidias Newsletter No. 6, pp. 3, 6, Jun. 2001. Retrieved from the Internet: URL:http://www.materialise.com/medical/files/pdf.

(Continued)

*Primary Examiner*—Pedro Philogene
(74) *Attorney, Agent, or Firm*—Bromberg & Sunstein LLP

(57) ABSTRACT

Disclosed herein are tools for repairing articular surfaces repair materials and for repairing an articular surface. The surgical tools are designed to be customizable or highly selectable by patient to increase the speed, accuracy and simplicity of performing total or partial arthroplasty.

80 Claims, 25 Drawing Sheets

U.S. PATENT DOCUMENTS

| | | | | |
|---|---|---|---|---|
| 4,052,753 A | 10/1977 | Dedo | | 3/1 |
| 4,055,862 A | 11/1977 | Farling | | 3/1.91 |
| 4,085,466 A | 4/1978 | Goodfellow et al. | | 3/1.91 |
| 4,203,444 A | 5/1980 | Bonnell et al. | | 128/176 |
| 4,340,978 A | 7/1982 | Buechel et al. | | 3/1.911 |
| 4,436,684 A | 3/1984 | White | | 264/138 |
| 4,502,161 A | 3/1985 | Wall | | 3/1.91 |
| 4,586,496 A | 5/1986 | Keller | | 128/92 |
| 4,601,290 A | 7/1986 | Effron et al. | | 128/305 |
| 4,609,551 A | 9/1986 | Caplan et al. | | 424/95 |
| 4,627,853 A | 12/1986 | Campbell et al. | | 623/16 |
| 4,721,104 A | 1/1988 | Kaufman et al. | | 128/92 |
| 4,769,040 A | 9/1988 | Wevers | | 623/20 |
| 4,841,975 A * | 6/1989 | Woolson | | 600/425 |
| 4,846,835 A | 7/1989 | Grande | | 623/11 |
| 4,865,607 A | 9/1989 | Witzel et al. | | 623/20 |
| 4,880,429 A | 11/1989 | Stone | | 623/18 |
| 5,041,138 A | 8/1991 | Vacanti et al. | | 623/16 |
| 5,059,216 A | 10/1991 | Winters | | 623/20 |
| 5,067,964 A | 11/1991 | Richmond et al. | | 623/18 |
| 5,129,908 A * | 7/1992 | Petersen | | 606/88 |
| 5,133,759 A | 7/1992 | Turner | | 623/20 |
| 5,154,717 A | 10/1992 | Matsen, III et al. | | 606/53 |
| 5,171,322 A | 12/1992 | Kenny | | 623/18 |
| 5,197,985 A | 3/1993 | Caplan et al. | | 623/549 |
| 5,206,023 A | 4/1993 | Hunziker | | 424/423 |
| 5,226,914 A | 7/1993 | Caplan et al. | | 623/549 |
| 5,234,433 A | 8/1993 | Bert et al. | | 606/88 |
| 5,258,032 A | 11/1993 | Bertin | | 623/20 |
| 5,270,300 A | 12/1993 | Hunziker | | 514/12 |
| 5,306,311 A | 4/1994 | Stone et al. | | 623/18 |
| 5,314,482 A | 5/1994 | Goodfellow et al. | | 623/20 |
| 5,368,858 A | 11/1994 | Hunziker | | 424/423 |
| 5,380,332 A | 1/1995 | Ferrante | | 606/79 |
| 5,468,787 A | 11/1995 | Braden et al. | | 523/113 |
| 5,474,559 A | 12/1995 | Bertin et al. | | 606/89 |
| 5,501,687 A | 3/1996 | Willert et al. | | 606/94 |
| 5,503,162 A | 4/1996 | Athanasiou et al. | | 128/774 |
| 5,540,696 A | 7/1996 | Booth, Jr. et al. | | 606/88 |
| 5,556,432 A | 9/1996 | Kubein-Messenburg et al. | | 623/20 |
| 5,597,379 A | 1/1997 | Haines et al. | | 606/80 |
| 5,601,563 A | 2/1997 | Burke et al. | | 606/86 |
| 5,632,745 A | 5/1997 | Schwartz | | 606/75 |
| 5,649,929 A | 7/1997 | Callaway | | 606/88 |
| 5,671,741 A | 9/1997 | Lang et al. | | 128/653 |
| 5,682,886 A | 11/1997 | Delp et al. | | 128/653.1 |
| 5,683,466 A | 11/1997 | Vitale | | 623/18 |
| 5,728,162 A | 3/1998 | Eckhoff | | 623/20 |
| 5,749,874 A | 5/1998 | Schwartz | | 606/75 |
| 5,749,876 A | 5/1998 | Duvillier et al. | | 606/88 |
| 5,768,134 A | 6/1998 | Swaelens et al. | | 364/468.28 |
| 5,769,899 A | 6/1998 | Schwartz et al. | | 623/18 |
| 5,786,217 A | 7/1998 | Tubo et al. | | 435/402 |
| 5,827,289 A | 10/1998 | Reiley et al. | | 606/86 |
| 5,835,619 A | 11/1998 | Morimoto et al. | | 382/132 |
| 5,840,443 A | 11/1998 | Gregg et al. | | 429/212 |
| 5,842,477 A | 12/1998 | Naughton et al. | | 128/898 |
| 5,853,746 A | 12/1998 | Hunziker | | 424/426 |
| 5,871,018 A | 2/1999 | Delp et al. | | 128/898 |
| 5,871,542 A | 2/1999 | Goodfellow et al. | | 623/20 |
| 5,871,546 A | 2/1999 | Colleran et al. | | 623/18 |
| 5,879,390 A | 3/1999 | Kubein-Meesenburg et al. | | 623/20 |
| 5,885,296 A | 3/1999 | Masini | | 606/86 |
| 5,885,298 A | 3/1999 | Herrington et al. | | 606/88 |
| 5,897,559 A | 4/1999 | Masini | | 606/86 |
| 5,900,245 A | 5/1999 | Sawhney et al. | | 424/426 |
| 5,906,934 A | 5/1999 | Grande et al. | | 435/325 |
| 5,911,723 A | 6/1999 | Ashby et al. | | 606/88 |
| 5,916,220 A * | 6/1999 | Masini | | 606/88 |
| 5,939,323 A | 8/1999 | Valentini et al. | | 435/395 |
| 5,961,523 A | 10/1999 | Masini | | 606/86 |
| 5,968,051 A | 10/1999 | Luckman et al. | | 606/88 |
| 5,972,385 A | 10/1999 | Liu et al. | | 424/486 |
| 6,007,537 A * | 12/1999 | Burkinshaw et al. | | 606/66 |
| 6,046,379 A | 4/2000 | Stone et al. | | 623/11 |
| 6,082,364 A | 7/2000 | Balian et al. | | 128/898 |
| 6,090,144 A | 7/2000 | Letot et al. | | 623/20 |
| 6,093,204 A | 7/2000 | Stone | | 623/14.12 |
| 6,102,916 A | 8/2000 | Masini | | 606/88 |
| 6,110,209 A | 8/2000 | Stone | | 623/16.11 |
| 6,120,541 A | 9/2000 | Johnson | | 623/14.12 |
| 6,126,690 A | 10/2000 | Ateshian et al. | | 623/18 |
| 6,139,578 A | 10/2000 | Lee et al. | | 623/16.11 |
| 6,156,069 A | 12/2000 | Amstutz | | 623/22.11 |
| 6,161,080 A | 12/2000 | Aouni-Ateshian et al. | | 703/11 |
| 6,187,010 B1 | 2/2001 | Masini | | 606/86 |
| 6,200,606 B1 | 3/2001 | Peterson et al. | | 424/574 |
| 6,203,546 B1 | 3/2001 | MacMahon | | 606/87 |
| 6,203,576 B1 | 3/2001 | Afriat et al. | | 623/20.27 |
| 6,206,927 B1 | 3/2001 | Fell et al. | | 623/20.29 |
| 6,214,369 B1 | 4/2001 | Grande et al. | | 424/423 |
| 6,217,894 B1 | 4/2001 | Sawhney et al. | | 424/426 |
| 6,219,571 B1 | 4/2001 | Hargreaves et al. | | 600/410 |
| 6,251,143 B1 | 6/2001 | Schwartz et al. | | 623/23.72 |
| 6,277,151 B1 | 8/2001 | Lee et al. | | 623/23.61 |
| 6,281,195 B1 | 8/2001 | Rueger et al. | | |
| 6,283,980 B1 | 9/2001 | Vibe-Hansen et al. | | 606/151 |
| 6,299,905 B1 | 10/2001 | Peterson et al. | | 424/486 |
| 6,328,765 B1 | 12/2001 | Hardwick et al. | | 623/23.72 |
| 6,344,043 B1 | 2/2002 | Pappas | | 606/96 |
| 6,344,059 B1 | 2/2002 | Krakovits et al. | | 623/20.21 |
| 6,352,558 B1 | 3/2002 | Spector | | 623/18.11 |
| 6,358,253 B1 | 3/2002 | Torrie et al. | | 606/96 |
| 6,371,958 B1 | 4/2002 | Overaker | | 606/72 |
| 6,375,658 B1 | 4/2002 | Hangody et al. | | 623/20.18 |
| 6,379,367 B1 | 4/2002 | Vibe-Hansen et al. | | 606/151 |
| 6,383,228 B1 | 5/2002 | Schmotzer | | 623/23.35 |
| 6,429,013 B1 | 8/2002 | Halvorsen et al. | | 435/377 |
| 6,443,988 B2 | 9/2002 | Felt et al. | | 623/17.12 |
| 6,444,222 B1 | 9/2002 | Asculai et al. | | 424/484 |
| 6,459,948 B1 | 10/2002 | Ateshian et al. | | 700/117 |
| 6,468,314 B2 | 10/2002 | Schwartz et al. | | 623/23.72 |
| 6,478,799 B1 | 11/2002 | Williamson | | 606/90 |
| 6,479,996 B1 | 11/2002 | Hoogeveen et al. | | 324/309 |
| 6,510,334 B1 | 1/2003 | Schuster et al. | | 600/407 |
| 6,520,964 B2 | 2/2003 | Tallarida et al. | | 606/71 |
| 6,558,421 B1 | 5/2003 | Fell et al. | | 623/14.12 |
| 6,560,476 B1 | 5/2003 | Pelletier et al. | | 600/410 |
| 6,575,980 B1 * | 6/2003 | Robie et al. | | 606/88 |
| 6,626,945 B2 | 9/2003 | Simon et al. | | 623/17.19 |
| 6,632,235 B2 | 10/2003 | Weikel et al. | | 606/192 |
| 6,652,587 B2 | 11/2003 | Felt et al. | | 623/20.16 |
| 6,679,917 B2 | 1/2004 | Ek | | 600/587 |
| 6,712,856 B1 | 3/2004 | Carignan et al. | | 623/20.35 |
| 6,905,514 B2 | 6/2005 | Carignan et al. | | 623/20.35 |
| 6,916,341 B2 | 7/2005 | Rolston | | 623/20.3 |
| 7,008,430 B2 | 3/2006 | Dong et al. | | 606/80 |
| 7,060,074 B2 | 6/2006 | Rosa et al. | | 606/88 |
| 7,104,997 B2 | 9/2006 | Lionberger et al. | | 606/88 |
| 7,115,131 B2 | 10/2006 | Engh et al. | | 606/79 |
| 7,117,027 B2 | 10/2006 | Zheng et al. | | 600/426 |
| 7,141,053 B2 * | 11/2006 | Rosa et al. | | 606/86 R |
| 7,184,814 B2 | 2/2007 | Lang et al. | | 600/416 |
| 7,239,908 B2 | 7/2007 | Alexander et al. | | 600/427 |
| 7,282,054 B2 | 10/2007 | Steffensmeier et al. | | 606/96 |
| 2001/0001120 A1 | 5/2001 | Masini | | 606/86 |
| 2001/0010023 A1 | 7/2001 | Schwartz et al. | | 623/23.72 |
| 2001/0039455 A1 | 11/2001 | Simon et al. | | 623/23.51 |
| 2002/0013626 A1 | 1/2002 | Geistlich et al. | | 623/23.57 |
| 2002/0029038 A1 | 3/2002 | Haines | | 606/54 |
| 2002/0045940 A1 | 4/2002 | Giannetti et al. | | 623/11.11 |
| 2002/0059049 A1 | 5/2002 | Bradbury et al. | | 703/11 |

| | | | | | | |
|---|---|---|---|---|---|---|
| 2002/0068979 | A1 | 6/2002 | Brown et al. ............... 623/20.3 | EP | 0814731 | 1/1996 |
| 2002/0082703 | A1 | 6/2002 | Repicci .................... 623/20.29 | EP | 0732091 | 3/1996 |
| 2002/0087274 | A1 | 7/2002 | Alexander et al. ........... 702/19 | EP | 0833620 | 6/1996 |
| 2002/0106625 | A1 | 8/2002 | Hung et al. ................. 435/1.1 | EP | 0896825 | 8/1997 |
| 2002/0115647 | A1 | 8/2002 | Halvorsen et al. .......... 514/171 | EP | 0809987 | 12/1997 |
| 2002/0120274 | A1 | 8/2002 | Overaker et al. ............. 606/72 | EP | 1077253 | 8/2000 |
| 2002/0120281 | A1 | 8/2002 | Overaker .................... 606/151 | EP | 1074229 | 2/2001 |
| 2002/0127264 | A1 | 9/2002 | Felt et al. .................... 424/423 | EP | 1129675 | 3/2001 |
| 2002/0133230 | A1 | 9/2002 | Repicci .................... 623/14.12 | EP | 1 132 061 | 9/2001 |
| 2002/0151986 | A1 | 10/2002 | Asculai et al. ............. 424/484 | EP | 1234552 | 2/2002 |
| 2002/0156150 | A1 | 10/2002 | Asculai et al. ........... 623/23.75 | EP | 1234555 | 2/2002 |
| 2002/0173852 | A1 | 11/2002 | Felt et al. ................. 623/20.32 | FR | 2 819 714 | 7/2002 |
| 2002/0183850 | A1 | 12/2002 | Felt et al. ................. 623/20.16 | GB | 2291355 | 1/1996 |
| 2003/0028196 | A1 | 2/2003 | Bonutti ....................... 606/87 | GB | 2348373 | 10/2000 |
| 2003/0055500 | A1 | 3/2003 | Fell et al. ................. 623/14.12 | JP | 1249049 | 3/1988 |
| 2003/0055501 | A1 | 3/2003 | Fell et al. ................. 623/14.12 | JP | 8173465 | 12/1994 |
| 2003/0055502 | A1 | 3/2003 | Lang et al. ............... 623/16.11 | JP | 9206322 | 2/1996 |
| 2003/0060882 | A1 | 3/2003 | Fell et al. ................. 623/14.12 | WO | WO 90/09769 | 9/1990 |
| 2003/0060883 | A1 | 3/2003 | Fell et al. ................. 623/14.12 | WO | WO 93/04710 | 3/1993 |
| 2003/0060884 | A1 | 3/2003 | Fell et al. ................. 623/14.12 | WO | WO 93/09819 | 5/1993 |
| 2003/0060885 | A1 | 3/2003 | Fell et al. ................. 623/14.12 | WO | WO 93/25157 | 12/1993 |
| 2003/0100907 | A1 | 5/2003 | Rosa et al. .................... 606/86 | WO | WO 95/27450 | 10/1995 |
| 2003/0100953 | A1 | 5/2003 | Rosa et al. .................. 623/20.3 | WO | WO 95/28688 | 10/1995 |
| 2003/0158558 | A1 | 8/2003 | Horn .......................... 606/87 | WO | WO 95/30390 | 11/1995 |
| 2003/0158606 | A1 | 8/2003 | Coon et al. ............... 623/20.15 | WO | WO 95/32623 | 12/1995 |
| 2003/0163137 | A1 | 8/2003 | Smucker et al. .............. 606/87 | WO | WO 96/24302 | 8/1996 |
| 2003/0216669 | A1 | 11/2003 | Lang et al. .................. 600/587 | WO | WO 97/25942 | 7/1997 |
| 2003/0225457 | A1 | 12/2003 | Justin et al. | WO | WO 97/26847 | 7/1997 |
| 2003/0236521 | A1 | 12/2003 | Brown et al. .................. 606/80 | WO | WO 97/38676 | 10/1997 |
| 2004/0098133 | A1 | 5/2004 | Carignan et al. .......... 623/20.15 | WO | WO 98/12994 | 4/1998 |
| 2004/0102852 | A1 | 5/2004 | Johnson et al. ........... 623/20.15 | WO | WO 98/30617 | 7/1998 |
| 2004/0122521 | A1 | 6/2004 | Lee et al. ................. 623/20.15 | WO | WO 99/02654 | 1/1999 |
| 2004/0133276 | A1 | 7/2004 | Lang et al. ............... 623/14.12 | WO | WO 99/08728 | 2/1999 |
| 2004/0138754 | A1 | 7/2004 | Lang et al. ............... 623/20.14 | WO | WO 99/42061 | 8/1999 |
| 2004/0147927 | A1 | 7/2004 | Tsougarakis et al. .......... 606/53 | WO | WO 99/47186 | 9/1999 |
| 2004/0153079 | A1 | 8/2004 | Tsougarakis et al. .......... 606/77 | WO | WO 99/51719 | 10/1999 |
| 2004/0153162 | A1 | 8/2004 | Sanford et al. ............. 623/20.3 | WO | WO 99/56674 | 11/1999 |
| 2004/0153164 | A1 | 8/2004 | Sanford et al. ........... 623/20.29 | WO | WO 00/09179 | 2/2000 |
| 2004/0167390 | A1 | 8/2004 | Alexander et al. .......... 600/410 | WO | WO 00/35346 | 6/2000 |
| 2004/0167630 | A1 | 8/2004 | Rolston .................. 623/20.14 | WO | WO 00/48550 | 8/2000 |
| 2004/0193280 | A1 | 9/2004 | Webster et al. ........... 623/20.33 | WO | WO 00/59411 | 10/2000 |
| 2004/0204644 | A1 | 10/2004 | Tsougarakis et al. ........ 600/410 | WO | WO 00/74554 | 12/2000 |
| 2004/0204760 | A1 | 10/2004 | Fitz et al. ................. 623/14.12 | WO | WO 01/10356 | 2/2001 |
| 2004/0236424 | A1 | 11/2004 | Berez et al. ............... 623/14.12 | WO | WO 01/17463 | 3/2001 |
| 2004/0249386 | A1 | 12/2004 | Faoro .......................... 606/88 | WO | WO 01/19254 | 3/2001 |
| 2004/0267390 | A1 | 12/2004 | Ben-Yaacov et al. .......... 700/94 | WO | WO 01/35968 | 5/2001 |
| 2005/0015153 | A1 | 1/2005 | Goble et al. .............. 623/23.46 | WO | WO 01/45764 | 6/2001 |
| 2005/0021039 | A1 | 1/2005 | Cusick et al. ................. 606/88 | WO | WO 01/68800 | 9/2001 |
| 2005/0043807 | A1 | 2/2005 | Wood ..................... 623/20.14 | WO | WO 01/70142 | 9/2001 |
| 2005/0085920 | A1 | 4/2005 | Williamson .............. 623/20.14 | WO | WO 01/91672 | 12/2001 |
| 2005/0107883 | A1 | 5/2005 | Goodfried et al. ......... 623/20.15 | WO | WO 02/22013 | 3/2002 |
| 2005/0107884 | A1 | 5/2005 | Johnson et al. ........... 623/20.15 | WO | WO 02/22014 | 3/2002 |
| 2005/0143745 | A1 | 6/2005 | Hodorek et al. .............. 606/87 | WO | WO 02/23483 | 3/2002 |
| 2005/0148843 | A1 | 7/2005 | Roose ....................... 600/407 | WO | WO 02/34310 | 5/2002 |
| 2005/0171612 | A1 | 8/2005 | Rolston .................. 623/20.19 | WO | WO 02/36147 | 5/2002 |
| 2005/0234461 | A1 | 10/2005 | Burdulis, Jr. et al. .......... 606/79 | WO | WO 02/006268 | 12/2002 |
| 2005/0267584 | A1 | 12/2005 | Burdulis, Jr. et al. ..... 623/20.19 | WO | WO 03/007788 | 1/2003 |
| 2006/0111722 | A1 | 5/2006 | Bouadi ....................... 606/79 | WO | WO 03/047470 | 6/2003 |
| 2006/0235421 | A1 | 10/2006 | Rosa et al. .................... 606/88 | WO | WO 03/051210 | 6/2003 |
| 2007/0015995 | A1 | 1/2007 | Lang et al. .................. 600/407 | WO | WO 2004/043305 | 5/2004 |
| 2007/0073305 | A1 | 3/2007 | Lionberger et al. ........... 606/87 | WO | WO 2004/049981 | 6/2004 |
| 2007/0118141 | A1 | 5/2007 | Marchyn et al. .............. 606/88 | WO | WO 2006/060795 | 6/2006 |
| 2007/0198022 | A1 | 8/2007 | Lang et al. .................... 606/88 | WO | WO 2007/092841 | 8/2007 |
| 2007/0203430 | A1 | 8/2007 | Lang et al. .................. 600/587 | | | |
| 2007/0276224 | A1 | 11/2007 | Lang et al. .................. 600/410 | | | |
| 2008/0015433 | A1 | 1/2008 | Alexander et al. .......... 600/427 | | | |

FOREIGN PATENT DOCUMENTS

| | | |
|---|---|---|
| EP | 0528080 | 8/1991 |
| EP | 0626156 | 1/1992 |
| EP | 0530804 | 9/1992 |
| EP | 0613380 | 11/1992 |

OTHER PUBLICATIONS

Kidder J. et al., "3D model acquisition, design, planning and manufacturing of orthopaedic devices: a framework", Proceedings of theSPIE—Advanced Sensor and Control-System Interface, Boston, MA, vol. 2911, pp. 9-22, Nov. 21, 1996.

Carr J.C. et al., "Surface Interpolation with Radial Basis Functions for Medical Imaging", IEEE Transactions on Medical Imaging, IEEE, Inc. New York, vol. 16, No. 1, Feb. 1, 1997, pp. 96-107.

C.S. Ranawat et al., "MacIntosh Hemiarthroplasty in Rheumatoid Knee" Acta Orthop Belg. Jan.-Feb. 1973: 39(1):102-112.

B. Blum et al., "Knee Arthroplasty in Patients with Rheumatoid Arthritis", Ann. Rheum. Dis. Jan. 1974: 33(1):1-11.

Nelson M.D. et al., "Arthroplasty and Arthrodesis of the Knee Joint", Orthop. Clin. North Am. Mar. 1971: 2(1):245-64.

McCollum et al., "Tibial Plateau Prosthesis in Arthroplasty of the Knee", J. Bone Joint Surg. Am. Jun. 1970:52(4):827-8.

Hastings D.E. et al., "Double Hemiarthroplasty of the Knee in Rheumatoid Arthritis. A Survey of Fifty Consecutive Cases", J. Bone Joint Surg. Br. Feb. 1973:55(1):112-118.

Schron, D. et al., "MacIntosh Arthroplasty in Rheumatoid Arthritis", Rheumatol Rehabil. Aug. 1978:17(3):155-163.

McKeever, D.C. et al., "The Classic Tibial Plateau Prosthesis", Clin. Orthop. Relat. Res. Jan.-Feb. 1985:(192):3-12.

Conaty et al., "Surgery of the Hip and Knee in Patients with Rheumatoid Arthritis", J. Bone Joint Surg. Am. Mar. 1973:55(2):301-314.

MacIntosh et al., "The Use of the Hemiarthroplasty Prosthesis for Advanced Osteoarthritis and Rheumatoid Arthritis of the Knee", J. of Bone & Joint Surg. 1972, vol. 54B, No. 2, pp. 244-255.

MacIntosh, "Arthroplasty of the Knee in Rheumatoid Arthritis Using the Hemiarthroplasty Prosthesis", Synovectomy and Arthroplasty in Rheumatoid Arthritis pp. 79-80, Second Int'l. Symposium, Jan. 27-29, 1967 (Basle, Switzerland).

MacIntosh, D.L., "Hemiarthroplasty of the Knee Using a Space Occupying Prosthesis for Painful Varus and Valgus Deformities", J. Bone Joint Surg. Am. Dec. 1958:40-A:1431.

Stauffer R. et al., "The MacIntosh Prosthesis. Prospective Clinical and Gait Eveluation", Arch. Surg. Jun. 1975:110(6):717-720.

Clary BB et al., "Experience with the MacIntosh Knee Prosthesis", South Med. J. Mar. 1972:65(3):265-272.

Ghelman MD, et al., "Kinematics of the Knee After Prosthetic Replacements", Clin. Orthop. May 1975: (108): 149-157.

Henderson, MD et al., "Experience with the Use of the Macintosh Prosthesis in Knees of Patients with Pheumatoid Arthritis", South. Med. J. Nov. 1969:62(11):1311-1315.

Potter M.D., "Arthroplasty of the Knee With Tibial Metallic Implants of the McKeever and MacIntosh Design", Sug. Clin. North Am. Aug. 1969:49(4):903-915.

Potter T.A., et al., "Arthroplasty of the Knee in Rheumatoid Arthritis and Osteoarthritis: A Follow-up Study After Implantation of the McKeever and MacIntosh Prostheses", J. Bone Joint Surg. Am. Jan. 1972:54(1):1-24.

Bogoch et al., "Supracondylar Fractures of the Femur Adjacent to Resurfacing and MacIntosh Arthroplasties of the Knee in Patients with Rheumatoid Arthritis", Clin. Orthop. Apr. 1988 (229):213-220.

Cameron et al., "Review of a Failed Knee Replacement and Some Observations on the Design of a Knee Resurfacing Prosthesis", Arch. Orthop Trauma Surg. 1980:97(2):87-89.

Kates A. et al., "Experiences of Arthroplasty of the Rheumatoid Knee Using MacIntosh Prostheses", Ann. Rheum. Dis. May 1969:28(3):328.

Jessop J.D. et al., "Follow-up of the MacIntosh Arthroplasty of the Knee Joint", Rheumatol Phys. Med. Feb. 1972: 11 (5): 217-224.

Andersson GB et al., "MacIntosh Arthroplasty In Rheumatoid Arthrisit", Acta. Orthrop. Scand. 1974:45 (2): 245-259.

Wordsworth et al., "MacIntosh Arthroplasty for the Rheumatoid Knee: A 10-year Follow Up", Ann. Rheum. Dis. Nov. 1985:44 (11): 738-741.

Kay N.R. et al., "MacIntosh Tibial Plateau Hemiprosthesis for the Rheumatoid Knee", J. Bone Joint Sur. Br. May 1972: 54(2): 256-262.

Porter M.L. et al., "MacIntosh Arthroplasty: a long-term review", J. R. Coll. Sur. Edinb. Jan.-Feb. 1988: (192): 199-201.

Vande Berg et al., "Assessment of Knee Cartilage in Cadavers with Dual-Detector Spiral CT Arthrography and MR Imaging", published online before print 10.1148/radiol.2222010597, Radiology 2002; 22: pp. 430-436.

MacIntosh, "Arthroplasty of The Knee in Rheumatoid Arthritis", Proceedings and Reports of councils and Associations, J. Bone & Joint Surg. (Feb. 1966), vol. 48B No. (1): 179.

Leenslag et al., "A Porous Composite for Reconstructioin of Meniscus Lesions", Biological and Biomechanical Performance of Biomaterials, Elsevier Science Publishers B.V., Amsterdam, 1986, pp. 147-152.

Platt et al., "Mould Arthroplasty of the Knee: A Ten-Year Follow-up Study", Oxford Regional Rheumatic Diseases Research Centre, J. of Bone and Joint Surg., vol. 51B, No. 1, Feb. 1969, pp. 76-87.

Stout et al., X-ray Structure Determination, a Practical Guide, Copyright 1968, Table of Contents.

Slone et al., Body CT, A Practical Approach, Coyright 2000, ISBN 0-07-058219-X, Table of Contents.

Lam et al., X-Ray Diagnosis: A Physician's Approach, ISBN 981-2083, 24-7, Index.

Tamez-Pena et al., MRI Isotropic Resolution Reconstruction from two Orthogonal Scans, Medical Imaging 2001: vol. 4322, pp. 87-97.

Brown, Ph.D. et al., MRI Basic Principals and Applications, 2$^{nd}$ Edition, A. John Wiley & Sons, Inc., 1955, table of contents.

Argenson et al., "Is There a Place for Patellofemoral Arthroplasty?", Clinical Orthopaedics and Related Research No. 321, pp. 162-167, 1995.

De Winter et al., "The Richards type 11 patellofemoral arthroplasty", Acta Orthop Scand 2001; 72 (5); 487-490.

International Search Report dated Feb. 23, 2005.

International Search Report dated May 13, 2005.

International Search Report dated Mar. 30, 2006.

International Searching Authority, International Search Report—International Application No. PCT/US2007/016181, together with Written Opinion of the International Searching Authority, mailed Sep. 7, 2007, received Sep. 10, 2007, 15 pages.

European Patent Office, Supplementary European Search Report—Application No. 04812187.5-2310, PCT/US2004/039616, dated Sep. 19, 2007, received Oct. 10, 2007, 3 pages.

Kshirsager et al. "Measurement Of Localised Cartilage Volume And Thickness Of Human Knee Joints By Computer Analysis Of Three-Dimensional Magnetic Resonance Images", Invest Radiol. 1998, pp. 1-33.

Office Action dated Jun. 15, 2007, pertaining to U.S. Appl. No. 09/882,363, 9 pages.

Response to Office Action dated Jun. 15, 2007, pertaining to U.S. Appl. No. 09/882,363, 12 pages.

Office Action dated Mar. 21, 2008, pertaining to U.S. Appl. No. 09/882,363, 12 pages.

Response to Office Action dated Jan. 30, 2007, pertaining to U.S. Appl. No. 09/882,363, 7 pages.

European Patent Office, European Search Report—Application No. EP 03 79 0194, dated Jul. 6, 2006, 5 pages.

* cited by examiner

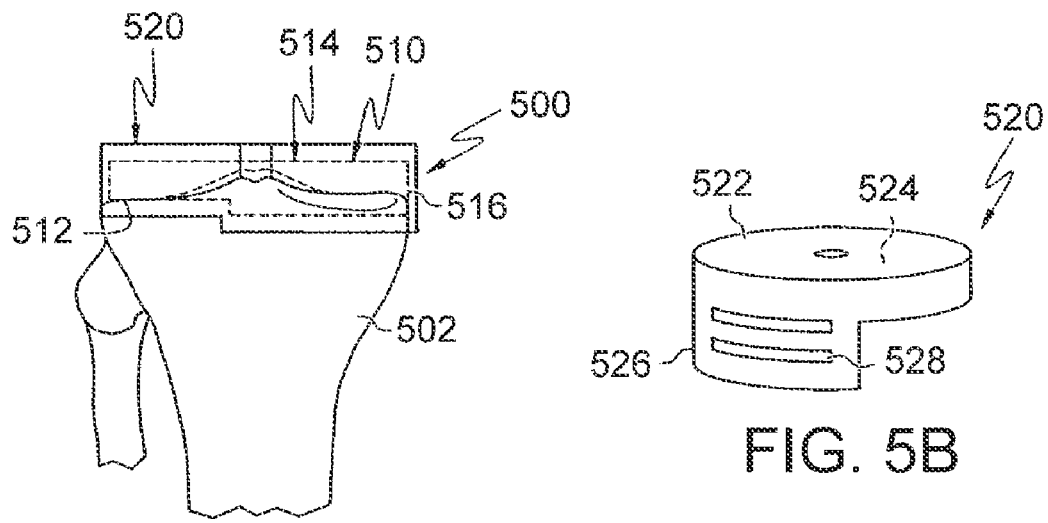
FIG. 5A
FIG. 5B
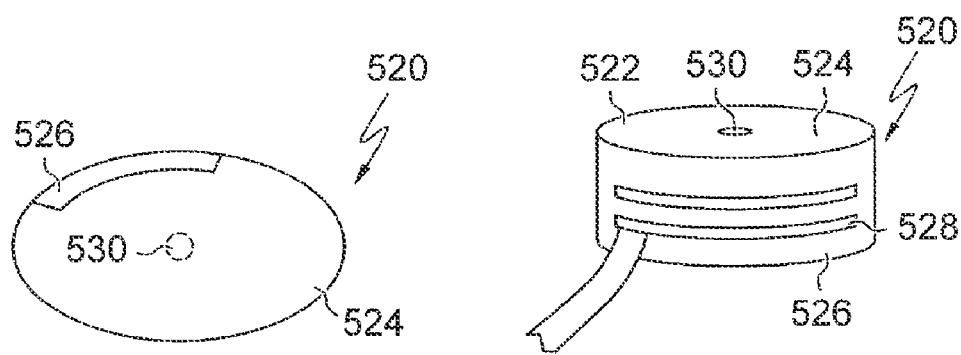
FIG. 5C
FIG. 5D
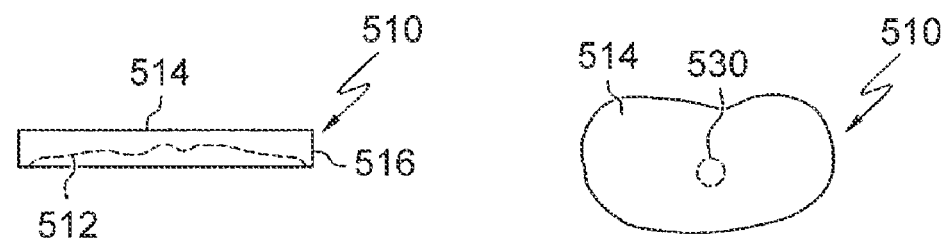
FIG. 5E
FIG. 5F

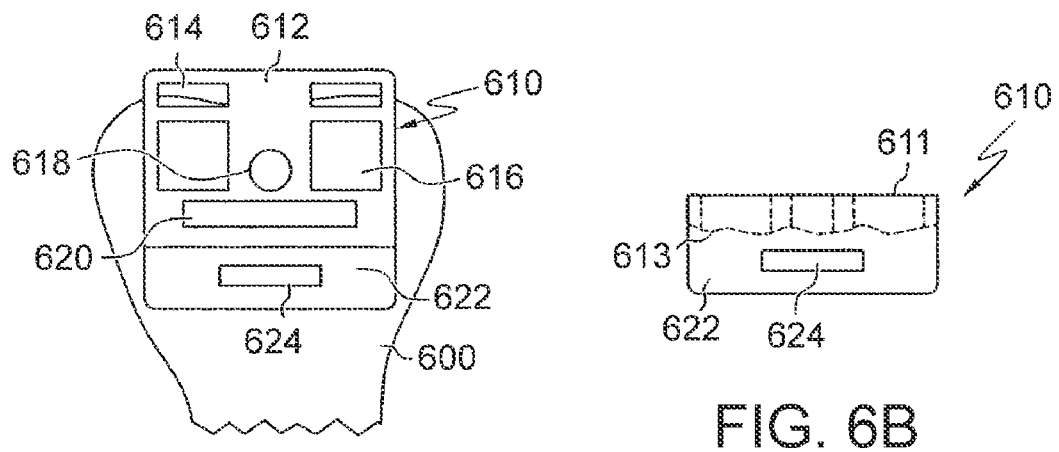
FIG. 6A
FIG. 6B
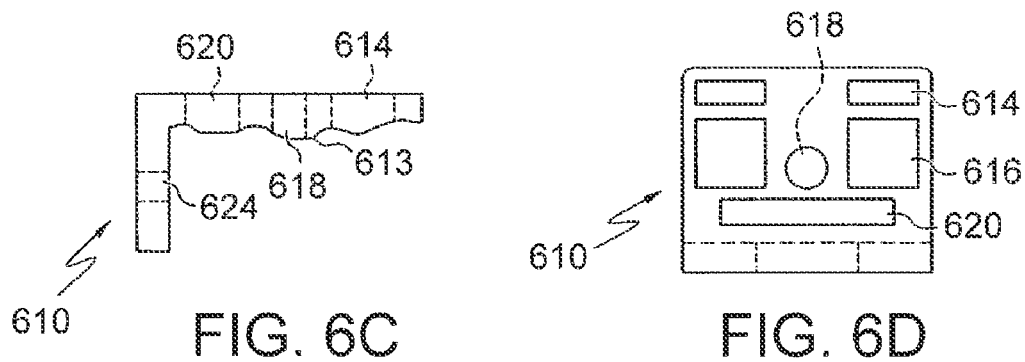
FIG. 6C
FIG. 6D

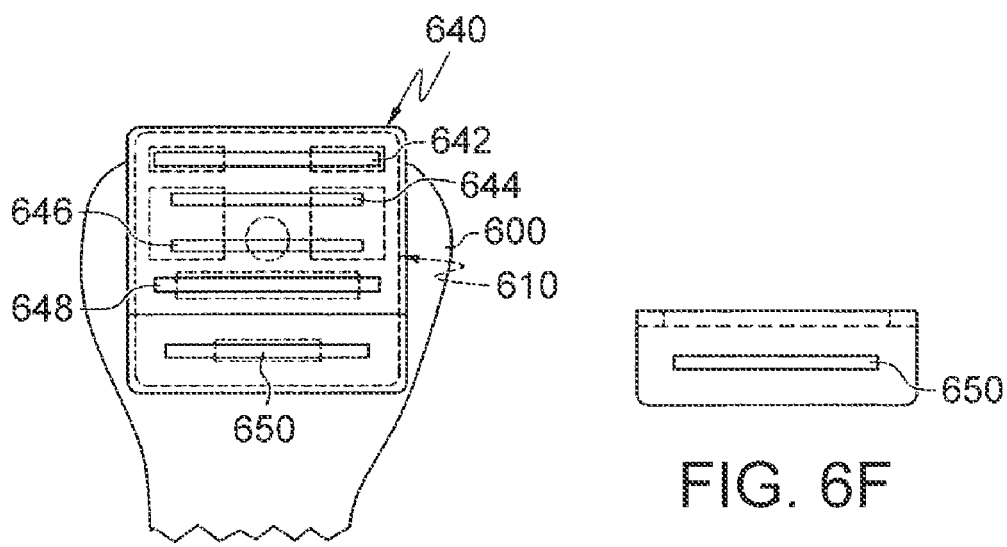
FIG. 6E
FIG. 6F
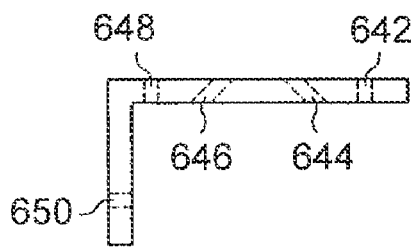
FIG. 6G
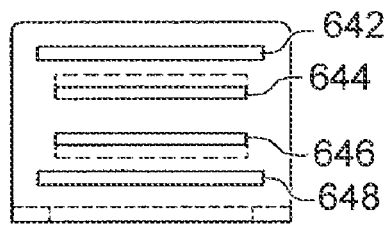
FIG. 6H
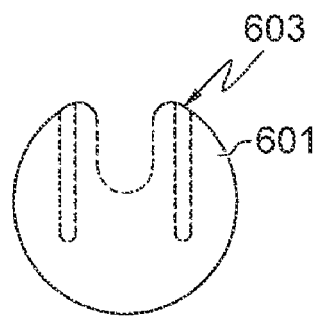
FIG. 6I

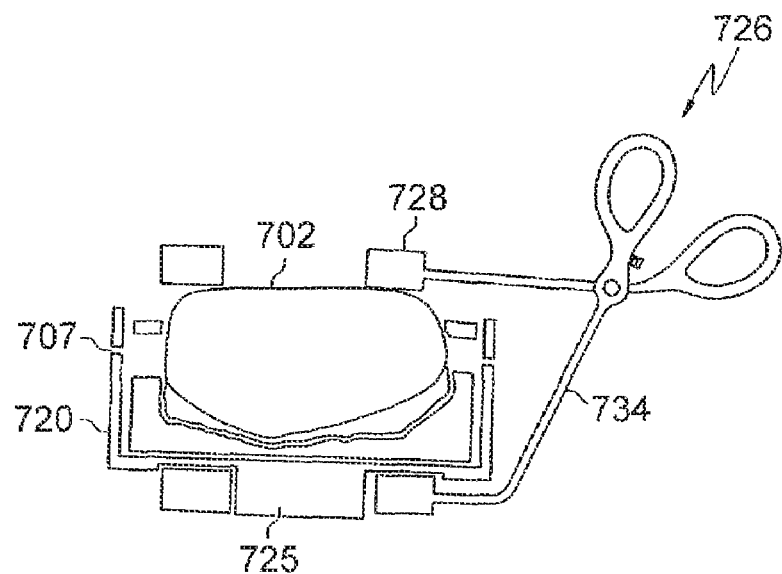
FIG. 7E
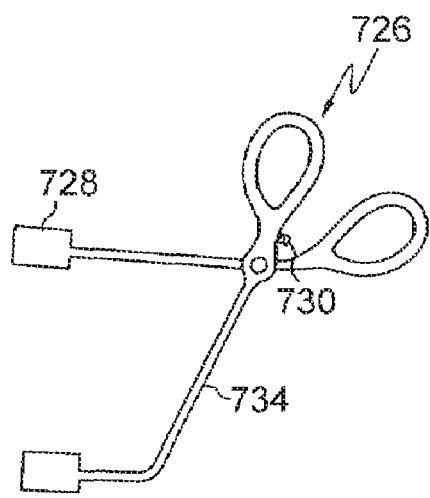
FIG. 7F
FIG. 7G

SURGICAL TOOLS FACILITATING INCREASED ACCURACY, SPEED AND SIMPLICITY IN PERFORMING JOINT ARTHROPLASTY

CROSS-REFERENCE TO RELATED APPLICATIONS

This application is a continuation-in-part of U.S. Ser. No. 10/724,010 for "PATIENT SELECTABLE JOINT ARTHROPLASTY DEVICES AND SURGICAL TOOLS FACILITATING INCREASED ACCURACY, SPEED AND SIMPLICITY IN PERFORMING TOTAL AND PARTIAL JOINT ARTHROPLASTY" filed Nov. 25, 2003 which is a continuation-in-part of U.S. Ser. No. 10/305,652 entitled "METHODS AND COMPOSITIONS FOR ARTICULAR REPAIR," filed Nov. 27, 2002, which is a continuation-in-part of U.S. Ser. No. 10/160,667, filed May 28, 2002, which in turn claims the benefit of U.S. Ser. No. 60/293,488 entitled "METHODS TO IMPROVE CARTILAGE REPAIR SYSTEMS", filed May 25, 2001, U.S. Ser. No. 60/363,527, entitled "NOVEL DEVICES FOR CARTILAGE REPAIR, filed Mar. 12, 2002 and U.S. Ser. Nos. 60/380,695 and 60/380,692, entitled "METHODS AND COMPOSITIONS FOR CARTILAGE REPAIR," and "METHODS FOR JOINT REPAIR,", filed May 14, 2002, all of which applications are hereby incorporated by reference in their entireties.

FIELD OF THE INVENTION

The present invention relates to methods, systems and devices for articular resurfacing. The present invention includes surgical molds designed to achieve optimal cut planes in a joint in preparation for installation of a joint implant.

BACKGROUND OF THE INVENTION

A variety of tools are available to assist surgeons in performing joint surgery. In the knee, for example, U.S. Pat. No. 4,501,266 to McDaniel issued Feb. 26, 1985 discloses a knee distraction device that facilitates knee arthroplasty. The device has an adjustable force calibration mechanism that enables the device to accommodate controlled selection of the ligament-tensioning force to be applied to the respective, opposing sides of the knee. U.S. Pat. No. 5,002,547 to Poggie et al. issued Mar. 26, 1991 discloses a modular apparatus for use in preparing the bone surface for implantation of a modular total knee prosthesis. The apparatus has cutting guides, templates, alignment devices along with a distractor and clamping instruments that provide modularity and facilitate bone resection and prosthesis implantation. U.S. Pat. No. 5,250,050 to Poggie et al. issued Oct. 5, 1993 is also directed to a modular apparatus for use in preparing a bone surface for the implantation of a modular total knee prosthesis. U.S. Pat. No. 5,387,216 to Thornhill et al. issued Feb. 7, 1995 discloses instrumentation for use in knee revision surgery. A bearing sleeve is provided that is inserted into the damaged canal in order to take up additional volume. The rod passes through the sleeve and is positioned to meet the natural canal of the bone. The rod is then held in a fixed position by the bearing sleeve. A cutting guide can then be mounted on the rod for cutting the bone and to provide a mounting surface for the implant. U.S. Pat. No. 6,056,756 to Eng et al. issued May 2, 2000 discloses a tool for preparing the distal femoral end for a prosthetic implant. The tool lays out the resection for prosthetic replacement and includes a jack for pivotally supporting an opposing bone such that the jack raises the opposing bone in flexion to the spacing of the intended prosthesis. U.S. Pat. No. 6,106,529 to Techiera issued Aug. 22, 2000 discloses an epicondylar axis referencing drill guide for use in resection to prepare a bone end for prosthetic joint replacement. U.S. Pat. No. 6,296,646 to Williamson issued Oct. 2, 2001 discloses a system that allows a practitioner to position the leg in the alignment that is directed at the end of the implant procedure and to cut both the femur and tibia while the leg is fixed in alignment. U.S. Pat. No. 6,620,168 to Lombardi et al. issued Sep. 16, 2003 discloses a tool for intermedullary revision surgery along with tibial components.

U.S. Pat. No. 5,578,037 to Sanders et al. issued Nov. 26, 1996 discloses a surgical guide for femoral resection. The guide enables a surgeon to resect a femoral neck during a hip arthroplasty procedure so that the femoral prosthesis can be implanted to preserve or closely approximate the anatomic center of rotation of the hip.

Currently available tools do not always enable the surgeon to make the most accurate cuts on the bone surface in preparing the target joint for implantation.

Thus, there remains a need for tools that improve the accuracy of the joint resurfacing process.

SUMMARY OF THE INVENTION

In an aspect of the invention, surgical tools for preparing a joint to receive an implant are described, for example a tool comprising one or more surfaces or members that conform at least partially to the shape of the articular surfaces of the joint (e.g., a femoral condyle and/or tibial plateau of a knee joint). In certain embodiments, the tool comprises Lucite silastic and/or other polymers or suitable materials. The tool can be re-useable or single-use. The tool can be comprised of a single component or multiple components. In certain embodiments, the tool comprises an array of adjustable, closely spaced pins.

The tool comprises: a mold having a surface for engaging a joint surface; a block that communicates with the mold; and at least one guide aperture in the block. Another tool is disclosed that is formed at least partially in situ and comprises: a mold formed in situ using at least one of an inflatable hollow device or a retaining device to conform to the joint surface on at least one surface having a surface for engaging a joint surface; a block that communicates with the mold; and at least one guide aperture in the block.

In any of the embodiments and aspects described herein, the joint can be a knee, shoulder, hip, vertebrae, elbow, ankle, wrist etc.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 7A-G illustrate patellar cutting blocks and molds used to prepare the patella for receiving a portion of a knee implant.

DETAILED DESCRIPTION OF THE INVENTION

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

As will be appreciated by those of skill in the art, the practice of the present invention employs, unless otherwise indicated, conventional methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. Such techniques are explained fully in the literature and need not be described herein. See, e.g., X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher. See also, The Essential Physics of Medical Imaging ($2^{nd}$ Ed.), Jerrold T. Bushberg, et al.

As described herein, repair systems, including surgical instruments, guides and molds, of various sizes, curvatures and thicknesses can be obtained. These repair systems, including surgical instruments, guides and molds, can be catalogued and stored to create a library of systems from which an appropriate system for an individual patient can then be selected. In other words, a defect, or an articular surface, is assessed in a particular subject and a pre-existing repair system, including surgical instruments, guides and molds, having a suitable shape and size is selected from the library for further manipulation (e.g., shaping) and implantation.

Performing a total knee arthroplasty is a complicated procedure. In replacing the knee with an artificial knee, it is important to get the anatomical and mechanical axes of the lower extremity aligned correctly to ensure optimal functioning of the implanted knee.

Figure 1A:
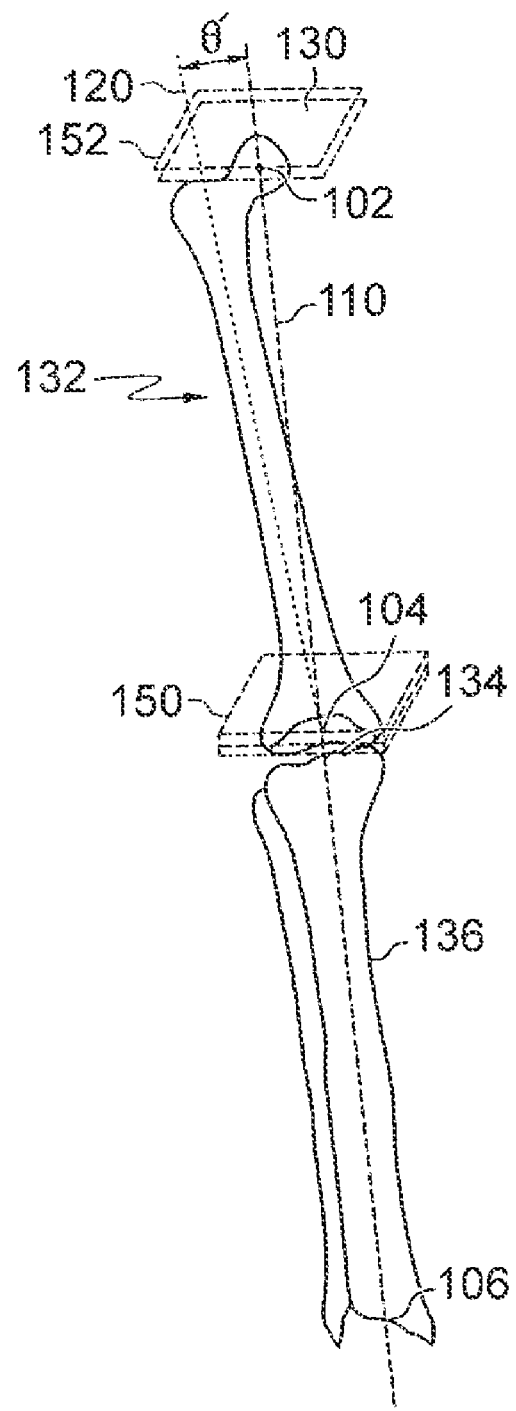
FIG. 1A illustrates a femur, tibia and fibula along with the mechanical and anatomic axes.

As shown in FIG. 1A, the center of the hip 102 (located at the head 130 of the femur 132), the center of the knee 104 (located at the notch where the intercondular tubercle 134 of the tibia 136 meet the femur) and ankle 106 lie approximately in a straight line 110 which defines the mechanical axis of the lower extremity. The anatomic axis 120 aligns 5-7° offset θ from the mechanical axis in the valgus, or outward, direction.

The long axis of the tibia 136 is collinear with the mechanical axis of the lower extremity 110. From a three-dimensional perspective, the lower extremity of the body ideally functions within a single plane known as the median anterior-posterior plane (MAP-plane) throughout the flexion-extension arc. In order to accomplish this, the femoral head 130, the mechanical axis of the femur, the patellar groove, the intercondylar notch, the patellar articular crest, the tibia and the ankle remain within the MAP-plane during the flexion-extension movement. During movement, the tibia rotates as the knee flexes and extends in the epicondylar axis which is perpendicular to the MAP-plane.

A variety of image slices can be taken at each individual joint, e.g., the knee joint $150$-$150_n$, and the hip joint $152$-$150_n$. These image slices can be used as described above in Section I along with an image of the full leg to ascertain the axis.

With disease and malfunction of the knee, alignment of the anatomic axis is altered. Performing a total knee arthroplasty is one solution for correcting a diseased knee. Implanting a total knee joint, such as the PFC Sigma RP Knee System by Johnson & Johnson, requires that a series of resections be made to the surfaces forming the knee joint in order to facilitate installation of the artificial knee. The resections should be made to enable the installed artificial knee to achieve flexion-extension movement within the MAP-plane and to optimize the patient's anatomical and mechanical axis of the lower extremity.

First, the tibia 130 is resected to create a flat surface to accept the tibial component of the implant. In most cases, the tibial surface is resected perpendicular to the long axis of the tibia in the coronal plane, but is typically sloped 4-7° posteriorly in the sagittal plane to match the normal slope of the tibia. As will be appreciated by those of skill in the art, the sagittal slope can be 0° where the device to be implanted does not require a sloped tibial cut. The resection line 158 is perpendicular to the mechanical axis 110, but the angle between the resection line and the surface plane of the plateau 160 varies depending on the amount of damage to the knee.

Figure 1B:
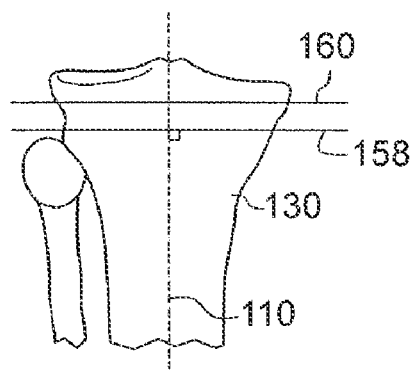
FIGS. 1B-E illustrate the tibia with the anatomic and mechanical axis used to create a cutting plane along with a cut femur and tibia.
Figure 1C:
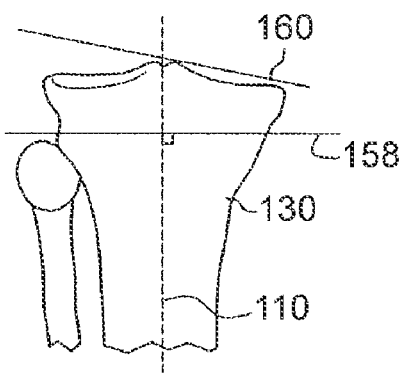
Figure 1D:
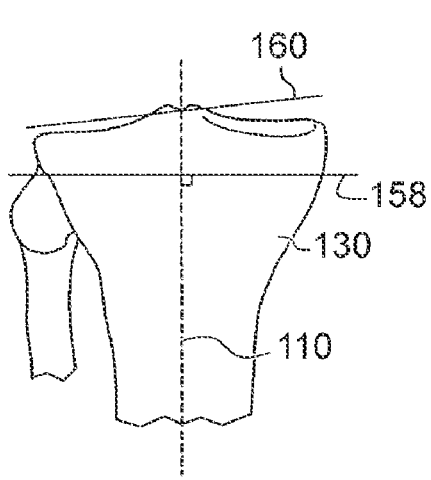

FIGS. 1B-D illustrate an anterior view of a resection of an anatomically normal tibial component, a tibial component in a varus knee, and a tibial component in a valgus knee, respectively. In each figure, the mechanical axis 110 extends vertically through the bone and the resection line 158 is perpendicular to the mechanical axis 110 and to the coronal plane, varying from the surface line formed by the joint depending on the amount of damage to the joint. FIG. 1B illustrates a normal knee wherein the line corresponding to the surface of the joint 160 is parallel to the resection line 158. FIG. 1C illustrates a varus knee wherein the line corresponding to the surface of the joint 160 is not parallel to the resection line 158. FIG. 1D illustrates a valgus knee wherein the line corresponding to the surface of the joint 160 is not parallel to the resection line 158.

Once the tibial surface has been prepared, the surgeon turns to preparing the femoral condyle.

The plateau of the femur 170 is resected to provide flat surfaces that communicate with the interior of the femoral prosthesis. The cuts made to the femur are based on the overall height of the gap to be created between the tibia and the femur. Typically, a 20 mm gap is desirable to provide the implanted prosthesis adequate room to achieve full range of motion. The bone is resected at a 5-7° angle valgus to the mechanical axis of the femur. Resected surface 172 forms a flat plane with an angular relationship to adjoining surfaces 174, 176. The angle θ', θ" between the surfaces 172-174, and 172-176 varies according to the design of the implant.

Figure 1E:
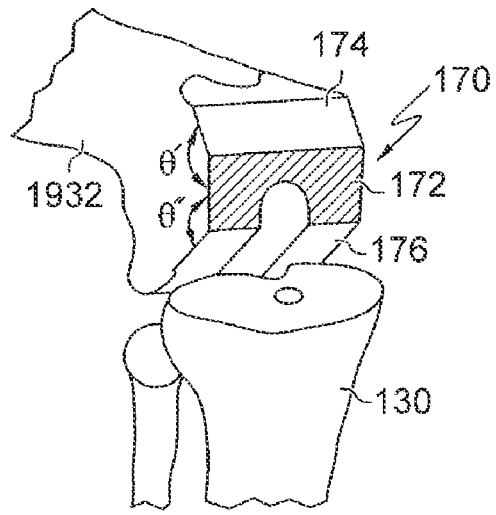
Figure 1F:
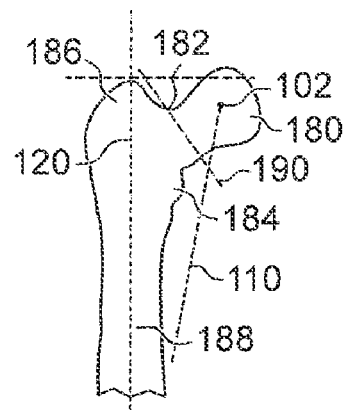
FIG. 1F illustrates the proximal end of the femur including the head of the femur.

As illustrated in FIG. 1F, the external geometry of the proximal femur includes the head 180, the neck 182, the lesser trochanter 184, the greater trochanter 186 and the proximal femoral diaphysis. The relative positions of the trochanters 184, 186, the femoral head center 102 and the femoral shaft 188 are correlated with the inclination of the neck-shaft angle. The mechanical axis 110 and anatomic axis 120 are also shown. Assessment of these relationships can change the reaming direction to achieve neutral alignment of the prosthesis with the femoral canal.

Using anteroposterior and lateral radiographs, measurements are made of the proximal and distal geometry to determine the size and optimal design of the implant.

Typically, after obtaining surgical access to the hip joint, the femoral neck 182 is resected, e.g. along the line 190. Once the neck is resected, the medullary canal is reamed. Reaming can be accomplished, for example, with a conical or straight reamer, or a flexible reamer. The depth of reaming is dictated by the specific design of the implant. Once the canal has been reamed, the proximal reamer is prepared by serial rasping, with the rasp directed down into the canal.

Further, surgical assistance can be provided by using a device applied to the outer surface of the articular cartilage or the bone, including the subchondral bone, in order to match the alignment of the articular repair system and the recipient site or the joint. The device can be round, circular, oval, ellipsoid, curved or irregular in shape. The shape can be selected or adjusted to match or enclose an area of diseased cartilage or an area slightly larger than the area of diseased cartilage or substantially larger than the diseased cartilage. The area can encompass the entire articular surface or the weight bearing surface. Such devices are typically preferred when replacement of a majority or an entire articular surface is contemplated.

Mechanical devices can be used for surgical assistance (e.g., surgical tools), for example using gels, molds, plastics or metal. One or more electronic images or intraoperative measurements can be obtained providing object coordinates that define the articular and/or bone surface and shape. These objects' coordinates can be utilized to either shape the device, e.g. using a CAD/CAM technique, to be adapted to a patient's articular anatomy or, alternatively, to select a typically premade device that has a good fit with a patient's articular anatomy. The device can have a surface and shape that will match all or portions of the articular or bone surface and shape, e.g. similar to a "mirror image." The device can include apertures, slots and/or holes to accommodate surgical instruments such as drills, reamers, curettes, k-wires, screws and saws.

Typically, a position will be chosen that will result in an anatomically desirable cut plane, drill hole, or general instrument orientation for subsequent placement of an articular repair system or for facilitating placement of the articular repair system. Moreover, the device can be designed so that the depth of the drill, reamer or other surgical instrument can be controlled, e.g., the drill cannot go any deeper into the tissue than defined by the device, and the size of the hole in the block can be designed to essentially match the size of the implant. Information about other joints or axis and alignment information of a joint or extremity can be included when selecting the position of these slots or holes. Alternatively, the openings in the device can be made larger than needed to accommodate these instruments. The device can also be configured to conform to the articular shape. The apertures, or openings, provided can be wide enough to allow for varying the position or angle of the surgical instrument, e.g., reamers, saws, drills, curettes and other surgical instruments. An instrument guide, typically comprised of a relatively hard material, can then be applied to the device. The device helps orient the instrument guide relative to the three-dimensional anatomy of the joint.

The surgeon can, optionally, make fine adjustments between the alignment device and the instrument guide. In this manner, an optimal compromise can be found, for example, between biomechanical alignment and joint laxity or biomechanical alignment and joint function, e.g. in a knee joint flexion gap and extension gap. By oversizing the openings in the alignment guide, the surgeon can utilize the instruments and insert them in the instrument guide without damaging the alignment guide. Thus, in particular if the alignment guide is made of plastic, debris will not be introduced into the joint. The position and orientation between the alignment guide and the instrument guide can be also be optimized with the use of, for example, interposed spacers, wedges, screws and other mechanical or electrical methods known in the art.

A surgeon may desire to influence joint laxity as well as joint alignment. This can be optimized for different flexion and extension, abduction, or adduction, internal and external rotation angles. For this purpose, for example, spacers can be introduced that are attached or that are in contact with one or more molds. The surgeon can intraoperatively evaluate the laxity or tightness of a joint using spacers with different thickness or one or more spacers with the same thickness. For example, spacers can be applied in a knee joint in the presence of one or more molds and the flexion gap can be evaluated with the knee joint in flexion. The knee joint can then be extended and the extension gap can be evaluated. Ultimately, the surgeon will select an optimal combination of spacers for a given joint and mold. A surgical cut guide can be applied to the mold with the spacers optionally interposed between the mold and the cut guide. In this manner, the exact position of the surgical cuts can be influenced and can be adjusted to achieve an optimal result. Someone skilled in the art will recognize other means for optimizing the position of the surgical cuts. For example, expandable or ratchet-like devices can be utilized that can be inserted into the joint or that can be attached or that can touch the mold. Hinge-like mechanisms are applicable. Similarly, jack-like mechanisms are useful. In principal, any mechanical or electrical device useful for fine-tuning the position of the cut guide relative to the molds can be used.

A surgeon may desire to influence joint laxity as well as joint alignment. This can be optimized for different flexion and extension, abduction, or adduction, internal and external rotation angles. For this purpose, for example, spacers can be introduced that are attached or that are in contact with one or more molds. The surgeon can intraoperatively evaluate the laxity or tightness of a joint using spacers with different thickness or one or more spacers with the same thickness. For example, spacers can be applied in a knee joint in the presence of one or more molds and the flexion gap can be evaluated with the knee joint in flexion. The knee joint can then be extended and the extension gap can be evaluated. Ultimately, the surgeon will select an optimal combination of spacers for a given joint and mold. A surgical cut guide can be applied to the mold with the spacers optionally interposed between the mold and the cut guide. In this manner, the exact position of the surgical cuts can be influenced and can be adjusted to achieve an optimal result. Someone skilled in the art will recognize other means for optimizing the position of the surgical cuts. For example, expandable or ratchet-like devices can be utilized that can be inserted into the joint or that can be attached or that can touch the mold. Hinge-like mechanisms are applicable. Similarly, jack-like mechanisms are useful. In principal, any mechanical or electrical device useful for fine-tuning the position of the cut guide relative to the molds can be used.

The molds and any related instrumentation such as spacers or ratchets can be combined with a tensiometer to provide a better intraoperative assessment of the joint. The tensiometer can be utilized to further optimize the anatomic alignment and tightness of the joint and to improve post-operative function and outcomes. Optionally local contact pressures may be evaluated intraoperatively, for example using a sensor like the ones manufactured by Tekscan, South Boston, Mass.

The mold or alignment guide can be made of a plastic or polymer. In other embodiments, the mold or portions of the mold can be made of metal. Metal inserts may be applied to plastic components. For example, a plastic mold may have an opening to accept a reaming device or a saw. A metal insert may be used to provide a hard wall to accept the reamer or saw. Using this or similar designs can be useful to avoid the accumulation of plastic or other debris in the joint when the saw or other surgical instruments may get in contact with the mold.

The molds may not only be used for assisting the surgical technique and guiding the placement and direction of surgical instruments. In addition, the molds can be utilized for guiding the placement of the implant or implant components. For example, in the hip joint, tilting of the acetabular component is a frequent problem with total hip arthroplasty. A mold can be applied to the acetabular wall with an opening in the center large enough to accommodate the acetabular component that the surgeon intends to place. The mold can have receptacles or notches that match the shape of small extensions that can be part of the implant or that can be applied to the implant. For example, the implant can have small members or extensions applied to the twelve o'clock and six o'clock positions. See, for example, FIG. 9A-D, discussed below. By aligning these members with notches or receptacles in the mold, the surgeon can ensure that the implant is inserted without tilting or rotation. These notches or receptacles can also be helpful to hold the implant in place while bone cement is hardening in cemented designs.

One or more molds can be used during the surgery. For example, in the hip, a mold can be initially applied to the proximal femur that closely approximates the 3D anatomy prior to the resection of the femoral head. The mold can include an opening to accommodate a saw (see FIGS. 8-9). The opening is positioned to achieve an optimally placed surgical cut for subsequent reaming and placement of the prosthesis. A second mold can then be applied to the proximal femur after the surgical cut has been made. The second mold can be useful for guiding the direction of a reamer prior to placement of the prosthesis. As can be seen in this, as well as in other examples, molds can be made for joints prior to any surgical intervention. However, it is also possible to make molds that are designed to fit to a bone or portions of a joint after the surgeon has already performed selected surgical procedures, such as cutting, reaming, drilling, etc. The mold can account for the shape of the bone or the joint resulting from these procedures.

In certain embodiments, the surgical assistance device comprises an array of adjustable, closely spaced pins (e.g., plurality of individually moveable mechanical elements). One or more electronic images or intraoperative measurements can be obtained providing object coordinates that define the articular and/or bone surface and shape. These objects' coordinates can be entered or transferred into the device, for example manually or electronically, and the information can be used to create a surface and shape that will match all or portions of the articular and/or bone surface and shape by moving one or more of the elements, e.g. similar to an "image." The device can include slots and holes to accommodate surgical instruments such as drills, cureftes, k-wires, screws and saws. The position of these slots and holes can be adjusted by moving one or more of the mechanical elements. Typically, a position will be chosen that will result in an anatomically desirable cut plane, reaming direction, or drill hole or instrument orientation for subsequent placement of an articular repair system or for facilitating the placement of an articular repair system. Information about other joints or axis and alignment information of a joint or extremity can be included when selecting the position of these slots or holes.

Figure 2:
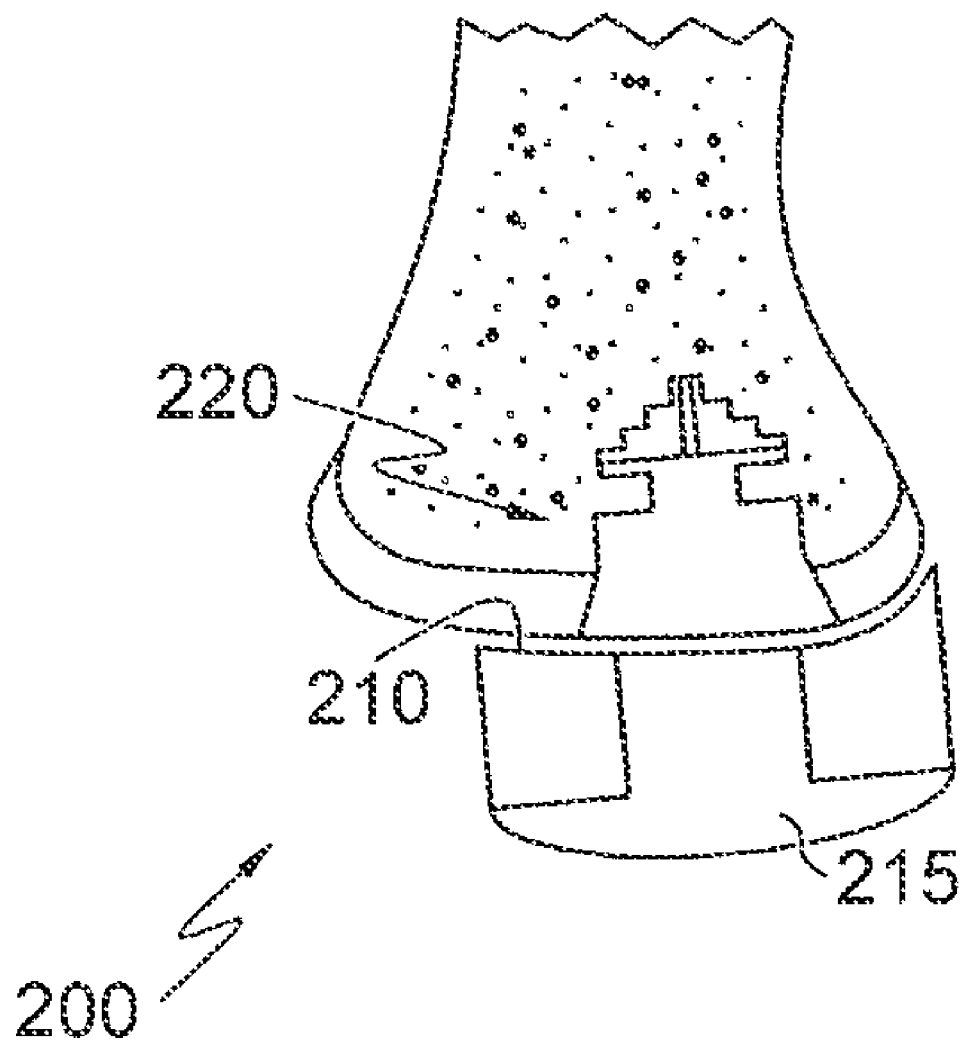
FIG. 2 shows an example of a surgical tool having one surface matching the geometry of an articular surface of the joint. Also shown is an aperture in the tool capable of controlling drill depth and width of the hole and allowing implantation of an insertion of implant having a press-fit design.

FIG. 2 shows an example of a surgical tool 200 having one surface 210 matching the geometry of an articular surface of the joint. Also shown is an aperture 215 in the tool 200 capable of controlling drill depth and width of the hole and allowing implantation or insertion of implant 220 having a press-fit design.

In another embodiment, a frame can be applied to the bone or the cartilage in areas other than the diseased bone or cartilage. The frame can include holders and guides for surgical instruments. The frame can be attached to one or preferably more previously defined anatomic reference points. Alternatively, the position of the frame can be cross-registered relative to one, or more, anatomic landmarks, using an imaging test or intraoperative measurement, for example one or more fluoroscopic images acquired intraoperatively. One or more electronic images or intraoperative measurements including using mechanical devices can be obtained providing object coordinates that define the articular and/or bone surface and shape. These objects' coordinates can be entered or transferred into the device, for example manually or electronically, and the information can be used to move one or more of the holders or guides for surgical instruments. Typically, a position will be chosen that will result in a surgically or anatomically desirable cut plane or drill hole orientation for subsequent placement of an articular repair system. Information about other joints or axis and alignment information of a joint or extremity can be included when selecting the position of these slots or holes.

Furthermore, re-useable tools (e.g., molds) can be also be created and employed. Non-limiting examples of re-useable materials include putties and other deformable materials (e.g., an array of adjustable closely spaced pins that can be configured to match the topography of a joint surface). In other embodiments, the molds may be made using balloons. The balloons can optionally be filled with a hardening material. A surface can be created or can be incorporated in the balloon that allows for placement of a surgical cut guide, reaming guide, drill guide or placement of other surgical tools. The balloon or other deformable material can be shaped intraoperatively to conform to at least one articular surface. Other surfaces can be shaped in order to be parallel or perpendicular to anatomic or biomechanical axes. The anatomic or biomechanical axes can be found using an intraoperative imaging test or surgical tools commonly used for this purpose in hip, knee or other arthroplasties.

In these embodiments, the mold can be created directly from the joint during surgery or, alternatively, created from an image of the joint, for example, using one or more computer programs to determine object coordinates defining the surface contour of the joint and transferring (e.g., dialing-in) these co-ordinates to the tool. Subsequently, the tool can be aligned accurately over the joint and, accordingly, the surgical instrument guide or the implant will be more accurately placed in or over the articular surface.

In both single-use and re-useable embodiments, the tool can be designed so that the instrument controls the depth and/or direction of the drill, i.e., the drill cannot go any deeper into the tissue than the instrument allows, and the size of the hole or aperture in the instrument can be designed to essentially match the size of the implant. The tool can be used for general prosthesis implantation, including, but not limited to, the articular repair implants described herein and for reaming the marrow in the case of a total arthroplasty.

These surgical tools (devices) can also be used to remove an area of diseased cartilage and underlying bone or an area slightly larger than the diseased cartilage and underlying bone. In addition, the device can be used on a "donor," e.g., a cadaveric specimen, to obtain implantable repair material. The device is typically positioned in the same general anatomic area in which the tissue was removed in the recipient. The shape of the device is then used to identify a donor site providing a seamless or near seamless match between the donor tissue sample and the recipient site. This ican be achieved by identifying the position of the device in which the articular surface in the donor, e.g. a cadaveric specimen, has a seamless or near seamless contact with the inner surface when applied to the cartilage.

The device can be molded, machined or formed based on the size of the area of diseased cartilage and based on the curvature of the cartilage or the underlying subchondral bone or a combination of both. The molding can take into consideration surgical removal of, for example, the meniscus, in arriving at a joint surface configuration. The device can then be applied to the donor, (e.g., a cadaveric specimen) and the donor tissue can be obtained with use of a blade or saw or other tissue removing device. The device can then be applied to the recipient in the area of the diseased cartilage and the diseased cartilage and underlying bone can be removed with use of a blade or saw or other tissue cutting device whereby the size and shape of the removed tissue containing the diseased cartilage will closely resemble the size and shape of the donor tissue. The donor tissue can then be attached to the recipient site. For example, said attachment can be achieved with use of screws or pins (e.g., metallic, non-metallic or bioresorable) or other fixation means including but not limited to a tissue adhesive. Attachment can be through the cartilage surface or alternatively, through the marrow space.

The implant site can be prepared with use of a robotic device. The robotic device can use information from an electronic image for preparing the recipient site.

Identification and preparation of the implant site and insertion of the implant can be supported by asurgical navigation system. In such a system, the position or orientation of a surgical instrument with respect to the patient's anatomy can be tracked in real-time in one or more 2D or 3D images. These 2D or 3D images can be calculated from images that were acquired preoperatively, such as MR or CT images. Non-image based surgical navigation systems that find axes or anatomical structures, for example with use of joint motion, can also be used. The position and orientation of the surgical instrument as well as the mold including alignment guides, surgical instrument guides, reaming guides, drill guides, saw guides, etc. can bedetermined from markers attached to these devices. These markers can be located by a detector using, for example, optical, acoustical or electromagnetic signals.

Identification and preparation of the implant site and insertion of the implant can also be supported with use of a C-arm system. The C-arm system can afford imaging of the joint in one or, preferably, multiple planes. The multiplanar imaging capability can aid in defining the shape of an articular surface. This information can be used to selected an implant with a good fit to the articular surface. Currently available C-arm systems also afford cross-sectional imaging capability, for example for identification and preparation of the implant site and insertion of the implant. C-arm imaging can be combined with administration of radiographic contrast.

The articular repair system, including surgical tools and instruments, molds, in situ repair systems, etc. can be formed or selected from a library or database of systems of various sizes, curvatures and thicknesses so that it will achieve a near anatomic fit or match with the surrounding or adjacent cartilage and/or subchondral bone. These systems can be premade or made to order for an individual patient. In order to control the fit or match of the articular repair system with the surrounding or adjacent cartilage or subchondral bone or menisci and other tissues preoperatively, a software program can be used that projects the articular repair system over the anatomic position where it will be implanted. Suitable software is commercially available and/or readily modified or designed by a skilled programmer.

In yet another embodiment, the articular surface repair system can be projected over the implantation site using one or more 3-D images. The cartilage and/or subchondral bone and other anatomic structures are extracted from a 3-D electronic image such as an MRI or a CT using manual, semi-automated and/or automated segmentation techniques. A 3-D representation of the cartilage and/or subchondral bone and other anatomic structures as well as the articular repair system is generated, for example using a polygon or NURBS surface or other parametric surface representation. For a description of various parametric surface representations see, for example Foley, J. D. et al., Computer Graphics: Principles and Practice in C; Addison-Wesley, 2.sup.nd edition, 1995).

The 3-D representations of the cartilage and/or subchondral bone and other anatomic structures and the articular repair system can be merged into a common coordinate system. The articular repair system, including surgical tools and instruments, molds, in situ repair systems, etc. can then be placed at the desired implantation site. The representations of the cartilage, subchondral bone, menisci and other anatomic structures and the articular repair system are rendered into a 3-D image, for example application programming interfaces (APIs) OpenGL.RTM. (standard library of advanced 3-D graphics functions developed by SGI, Inc.; available as part of the drivers for PC-based video cards, for example from www.nvidia.com for NYIDIA video cards or www.3dlabs.com for 3Dlabs products, or as part of the system software for Unix workstations) or DirectX.RTM. (multimedia API for Microsoft Windows.RTM. based PC systems; available from www.microsoft.com). The 3-D image can be rendered showing the cartilage, subchondral bone, menisci or other anatomic objects, and the articular repair system from varying angles, e.g. by rotating or moving them interactively or non-interactively, in real-time or non-real-time.

The software can be designed so that the articular repair system, including surgical tools and instruments, molds, in situ repair systems, etc. with the best fit relative to the cartilage and/or subchondral bone is automatically selected, for example using some of the techniques described above. Alternatively, the operator can select an articular repair system, including surgical tools and instruments, molds, in situ repair systems, etc. and project it or drag it onto the implantation site using suitable tools and techniques. The operator can move and rotate the articular repair systems in three dimensions relative to the implantation site and can perform a visual inspection of the fit between the articular repair system and the implantation site. The visual inspection can be computer assisted. The procedure can be repeated until a satisfactory fit has been achieved. The procedure can be performed manually by the operator; or it can be computer-assisted in whole or part. For example, the software can select a first trial implant that the operator can test. The operator can evaluate the fit. The software can be designed and used to highlight areas of poor alignment between the implant and the surrounding cartilage or subchondral bone or menisci or other tissues. Based on this information, the software or the operator can then select another implant and test its alignment. One of skill in the art will readily be able to select, modify and/or create suitable computer programs for the purposes described herein.

In another embodiment, the implantation site can be visualized using one or more cross-sectional 2-D images. Typically, a series of 2-D cross-sectional images will be used. The 2-D images can be generated with imaging tests such as CT, MRI, digital tomosynthesis, ultrasound, or optical coherence tomography using methods and tools known to those of skill in the art. The articular repair system, including surgical tools and instruments, molds, in situ repair systems, etc. can then be superimposed onto one or more of these 2-D images. The 2-D cross-sectional images can be reconstructed in other planes, e.g. from sagittal to coronal, etc. Isotropic data sets (e.g., data sets where the slice thickness is the same or nearly the same as the in-plane resolution) or near isotropic data sets can also be used. Multiple planes can be displayed simultaneously, for example using a split screen display. The operator can also scroll through the 2-D images in any desired orientation in real time or near real time; the operator can rotate the imaged tissue volume while doing this. The articular repair system, including surgical tools and instruments, molds, in situ repair systems, etc. can be displayed in cross-section utilizing different display planes, e.g. sagittal, coronal or axial, typically matching those of the 2-D images demonstrating the cartilage, subchondral bone, menisci or other tissue. Alternatively, a three-dimensional display can be used for the articular repair system. The 2-D electronic image and the 2-D or 3-D representation of the articular repair system, including surgical tools and instruments, molds, in situ repair systems, etc. can be merged into a common coordinate system. The articular repair system can then be placed at the desired implantation site. The series of 2-D cross-sections of the anatomic structures, the implantation site and the articular repair system can be displayed interactively (e.g. the operator can scroll through a series of slices) or non-interactively (e.g. as an animation that moves through the series of slices), in real-time or non-real-time.

The software can be designed so that the articular repair system, including surgical tools and instruments, molds, in situ repair systems, etc. with the best fit relative to the cartilage and/or subchondral bone is automatically selected, for example using one or more of the techniques described above. Alternatively, the operator can select an articular repair system, including surgical tools and instruments, molds, in situ repair systems, etc. and project it or drag it onto the implantation site displayed on the cross-sectional 2-D images. The operator can then move and rotate the articular repair system relative to the implantation site and scroll through a cross-sectional 2-D display of the articular repair system and of the anatomic structures. The operator can perform a visual and/or computer-assisted inspection of the fit between the articular repair system and the implantation site. The procedure can be repeated until a satisfactory fit has been achieved. The procedure can be entirely manual by the operator; it can, however, also be computer-assisted. For example, the software can select a first trial implant that the operator can test (e.g., evaluate the fit). Software that highlights areas of poor alignment between the implant and the surrounding cartilage or subchondral bone or menisci or other tissues can also be designed and used. Based on this information, the software or the operator can select another implant and test its alignment.

In still other embodiments, the surgical devices described herein can include one or more materials that harden to form a mold of the articular surface. A wide-variety of materials that harden in situ have been described above including polymers that can be triggered to undergo a phase change, for example polymers that are liquid or semi-liquid and harden to solids or gels upon exposure to air, application of ultraviolet light, visible light, exposure to blood, water or other ionic changes. (See, also, U.S. Pat. No. 6,443,988 to Felt et al. issued Sep. 3, 2002 and documents cited therein). Non-limiting examples of suitable curable and hardening materials include polyurethane materials (e.g., U.S. Pat. No. 6,443,988 to Felt et al., U.S. Pat. No. 5,288,797 to Khalil issued Feb. 22, 1994, U.S. Pat. No. 4,098,626 to Graham et al. issued Jul. 4, 1978 and U.S. Pat. No. 4,594,380 to Chapin et al. issued Jun. 10, 1986; and Lu et al. (2000) *BioMaterials* 21(15):1595-1605 describing porous poly(L-lactide acid foams); hydrophilic polymers as disclosed, for example, in U.S. Pat. No. 5,162,430; hydrogel materials such as those described in Wake et al. (1995) *Cell Transplantation* 4(3):275-279, Wiese et al. (2001) *J. Biomedical Materials Research* 54(2):179-188 and Marler et al. (2000) *Plastic Reconstruct. Surgery* 105(6):2049-2058; hyaluronic acid materials (e.g., Duranti et al. (1998) *Dermatologic Surgery* 24(12):1317-1325); expanding beads such as chitin beads (e.g., Yusof et al. (2001) *J. Biomedical Materials Research* 54(1):59-68); crystal free metals such as Liquidmetals®, and/or materials used in dental applications (See, e.g., Brauer and Antonucci, "Dental Applications" pp. 257-258 in "Concise Encyclopedia of Polymer Science and Engineering" and U.S. Pat. No. 4,368,040 to Weissman issued January 11, 1983). Any biocompatible material that is sufficiently flowable to permit it to be delivered to the joint and there undergo complete cure in situ under physiologically acceptable conditions can be used. The material can also be biodegradable.

The curable materials can be used in conjunction with a surgical tool as described herein. For example, the surgical tool can include one or more apertures therein adapted to receive injections and the curable materials can be injected through the apertures. Prior to solidifying in situ the materials will conform to the articular surface facing the surgical tool and, accordingly, will form a mirror image impression of the surface upon hardening, thereby recreating a normal or near normal articular surface. In addition, curable materials or surgical tools can also be used in conjunction with any of the imaging tests and analysis described herein, for example by molding these materials or surgical tools based on an image of a joint.

Figure 3:
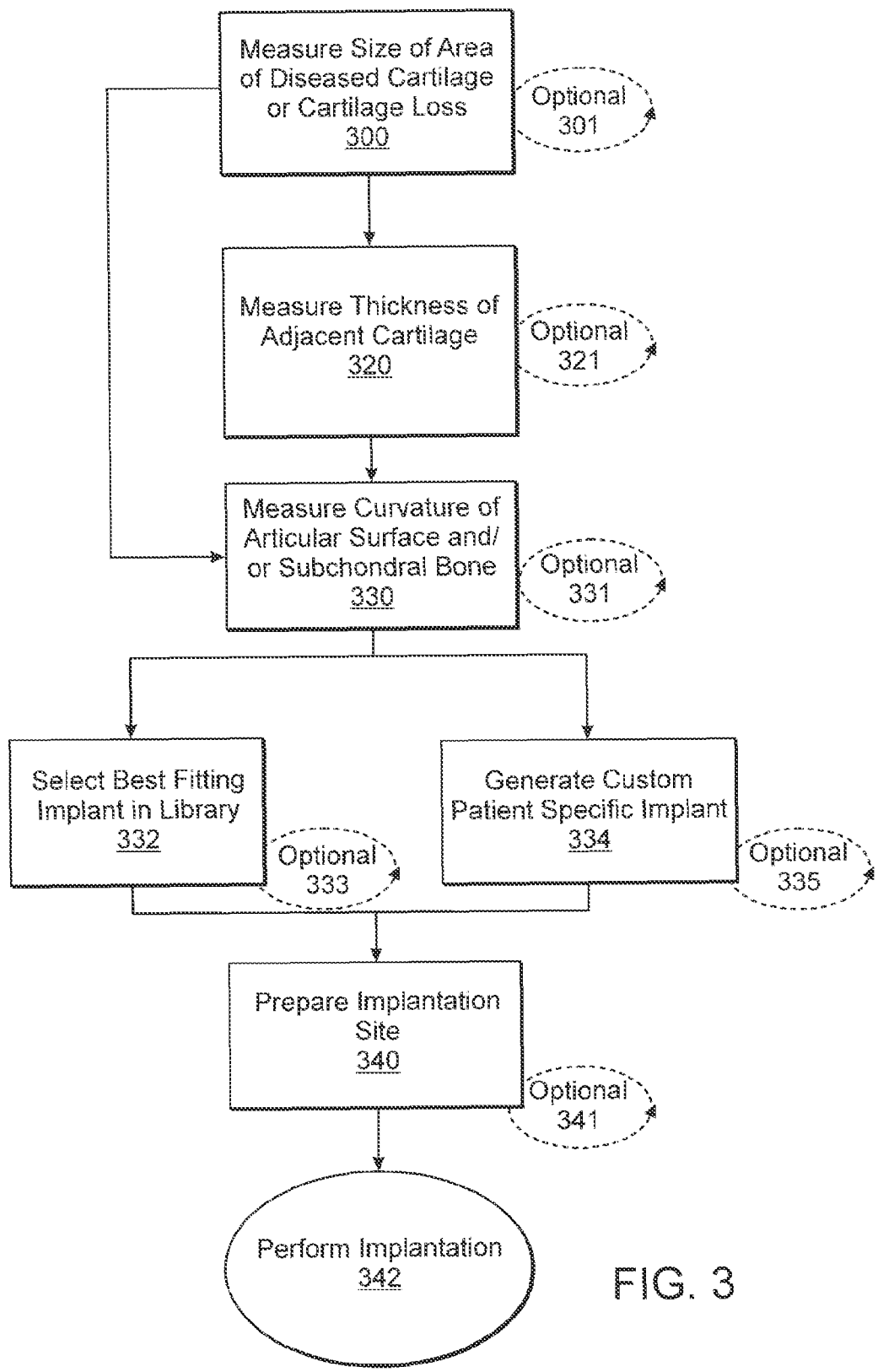
FIG. 3 is a flow chart depicting various methods of the invention used to create a mold for preparing a patient's joint for arthroscopic surgery.

FIG. 3 is a flow chart illustrating the steps involved in designing a mold for use in preparing a joint surface. Typically, the first step is to measure the size of the area of the diseased cartilage or cartilage loss 300, Once the size of the cartilage loss has been measured, the user can measure the thickness of the adjacent cartilage 320, prior to measuring the curvature of the articular surface and/or the subchondral bone 330. Alternatively, the user can skip the step of measuring the thickness of the adjacent cartilage 302. Once an understanding and determination of the nature of the cartilage defect is determined, either a mold can be selected from a library of molds 332 or a patient specific mold can be generated 334. In either event, the implantation site is then prepared 340 and implantation is performed 342. Any of these steps can be repeated by the optional repeat steps 301, 321, 331, 333, 335, 341.

A variety of techniques can be used to derive the shape of the mold. For example, a few selected CT slices through the hip joint, along with a full spiral CT through the knee joint and a few selected slices through the ankle joint can be used to help define the axes if surgery is contemplated of the knee joint. Once the axes are defined, the shape of the subchondral bone can be derived, followed by applying standardized cartilage loss. Other more sophisticated scanning procedures can be used to derive this information without departing from the scope of the invention.

Turning now to tools for specific joint applications which are intended to teach the concept of the design as it would then apply to other joints in the body:

When a total knee arthroplasty is contemplated, the patient can undergo an imaging test, as discussed in more detail above, that will demonstrate the articular anatomy of a knee joint, e.g. width of the femoral condyles, the tibial plateau etc. Additionally, other joints can be included in the imaging test thereby yielding information on femoral and tibial axes, deformities such as varus and valgus and other articular alignment. The imaging test can be an x-ray image, preferably in standing, load-bearing position, a CT scan or an MRI scan or combinations thereof. The articular surface and shape as well as alignment information generated with the imaging test can be used to shape the surgical assistance device, to select the surgical assistance device from a library of different devices with pre-made shapes and sizes, or can be entered into the surgical assistance device and can be used to define the preferred location and orientation of saw guides or drill holes or guides for reaming devices or other surgical instruments. Intraoperatively, the surgical assistance device is applied to the tibial plateau and subsequently the femoral condyle(s) by matching its surface with the articular surface or by attaching it to anatomic reference points on the bone or cartilage. The surgeon can then introduce a reamer or saw through the guides and prepare the joint for the implantation. By cutting the cartilage and bone along anatomically defined planes, a more reproducible placement of the implant can be achieved. This can ultimately result in improved postoperative results by optimizing biomechanical stresses applied to the implant and surrounding bone for the patient's anatomy and by minimizing axis malalignment of the implant. In addition, the surgical assistance device can greatly reduce the number of surgical instruments needed for total or unicompartmental knee arthroplasty. Thus, the use of one or more surgical assistance devices can help make joint arthroplasty more accurate, improve postoperative results, improve long-term implant survival, reduce cost by reducing the number of surgical instruments used. Moreover, the use of one or more surgical assistance device can help lower the technical difficulty of the procedure and can help decrease operating room ("OR") times.

Thus, surgical tools described herein can also be designed and used to control drill alignment, depth and width, for example when preparing a site to receive an implant. For example, the tools described herein, which typically conform to the joint surface, can provide for improved drill alignment and more accurate placement of any implant. An anatomically correct tool can be constructed by a number of methods and can be made of any material, preferably a translucent material such as plastic, Lucite, silastic, SLA or the like, and typically is a block-like shape prior to molding.

Figure 4A:
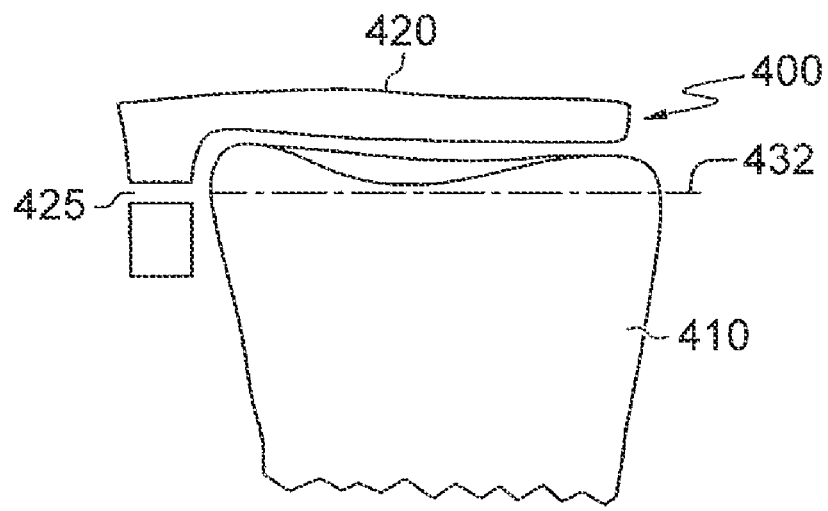
FIG. 4A depicts, in cross-section, an example of a surgical tool containing an aperture through which a surgical drill or saw can fit. The aperture guides the drill or saw to make the proper hole or cut in the underlying bone. Dotted lines represent where the cut corresponding to the aperture will be made in bone.

FIG. 4A depicts, in cross-section, an example of a mold 400 for use on the tibial surface having an upper surface 420. The mold 400 contains an aperture 425 through which a surgical drill or saw can fit. The aperture guides the drill or saw to make the proper hole or cut in the underlying bone 410 as illustrated in FIGS. 1B-D. Dotted lines 432 illustrate where the cut corresponding to the aperture will be made in bone.

Figure 4B:
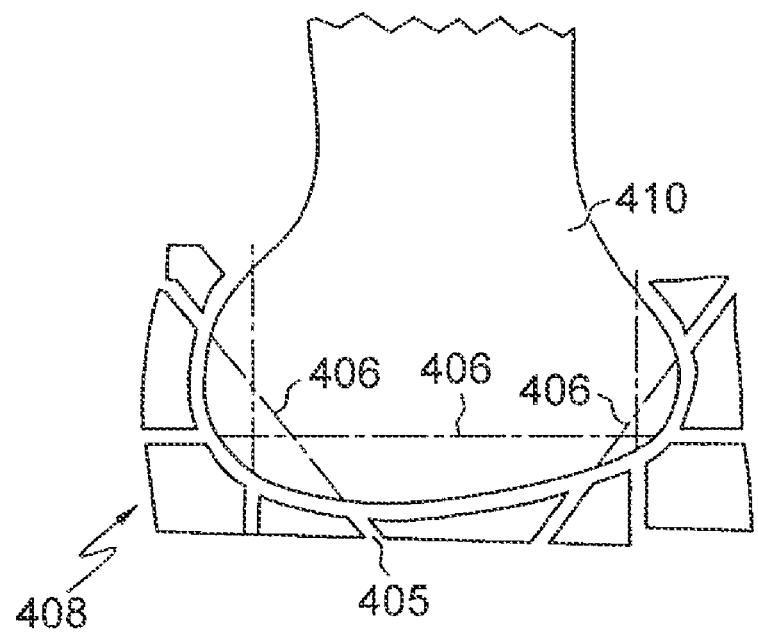
FIG. 4B depicts, in cross-section, an example of a surgical tool containing apertures through which a surgical drill or saw can fit and which guide the drill or saw to make cuts or holes in the bone. Dotted lines represent where the cuts corresponding to the apertures will be made in bone.

FIG. 4B depicts, a mold 408 suitable for use on the femur. As can be appreciated from this perspective, additional apertures are provided to enable additional cuts to the bone surface. The apertures 405 enable cuts 406 to the surface of the femur. The resulting shape of the femur corresponds to the shape of the interior surface of the femoral implant, typically as shown in FIG. 1E. Additional shapes can be achieved, if desired, by changing the size, orientation and placement of the apertures. Such changes would be desired where, for example, the interior shape of the femoral component of the implant requires a different shape of the prepared femur surface.

Turning now to FIG. 5, a variety of illustrations are provided showing a tibial cutting block and mold system. FIG. 5A illustrates the tibial cutting block 500 in conjunction with a tibia 502 that has not been resected. In this depiction, the cutting block 500 consists of at least two pieces. The first piece is a patient specific interior piece 510 or mold that is designed on its inferior surface 512 to mate, or substantially mate, with the existing geography of the patient's tibia 502. The superior surface 514 and side surfaces 516 of the first piece 510 are configured to mate within the interior of an exterior piece 520. The reusable exterior piece 520 fits over the interior piece 510. The system can be configured to hold the mold onto the bone.

The reusable exterior piece has a superior surface 522 and an inferior surface 524 that mates with the first piece 510. The reusable exterior piece 520 includes cutting guides 528, to assist the surgeon in performing the tibial surface cut described above. As shown herein a plurality of cutting guides can be provided to provide the surgeon a variety of locations to choose from in making the tibial cut. If necessary, additional spacers can be provided that fit between the first patient configured, or molded, piece 510 and the second reusable exterior piece, or cutting block, 520.

The variable nature of the interior piece facilitates obtaining the most accurate cut despite the level of disease of the joint because it positions the exterior piece 520 such that it can achieve a cut that is perpendicular to the mechanical axis. Either the interior piece 510 or the exterior piece 520 can be formed out of any of the materials discussed above in Section II, or any other suitable material. Additionally, a person of skill in the art will appreciate that the invention is not limited to the two piece configuration described herein. The reusable exterior piece 520 and the patient specific interior piece 510 can be a single piece that is either patient specific (where manufacturing costs of materials support such a product) or is reusable based on a library of substantially defect conforming shapes developed in response to known or common tibial surface sizes and defects.

The interior piece 510 is typically molded to the tibia including the subchondral bone and/or the cartilage. The surgeon will typically remove any residual meniscal tissue prior to applying the mold. Optionally, the interior surface 512 of the mold can include shape information of portions or all of the menisci.

Turning now to FIG. 5B-D, a variety of views of the removable exterior piece 520. The top surface 522 of the exterior piece can be relatively flat. The lower surface 524 which abuts the interior piece conforms to the shape of the upper surface of the interior piece. In this illustration the upper surface of the interior piece is flat, therefore the lower surface 524 of the reusable exterior surface is also flat to provide an optimal mating surface.

A guide plate 526 is provided that extends along the side of at least a portion of the exterior piece 520. The guide plate 526 provides one or more slots or guides 528 through which a saw blade can be inserted to achieve the cut desired of the tibial surface. Additionally, the slot, or guide, can be configured so that the saw blade cuts at a line perpendicular to the mechanical axis, or so that it cuts at a line that is perpendicular to the mechanical axis, but has a 4-7° slope in the sagittal plane to match the normal slope of the tibia.

Optionally, a central bore 530 can be provided that, for example, enables a drill to ream a hole into the bone for the stem of the tibial component of the knee implant.

Figure 5G:
FIGS. 5A-Q illustrate tibial cutting blocks and molds used to create a surface perpendicular to the anatomic axis for receiving the tibial portion of a knee implant.
Figure 5G:
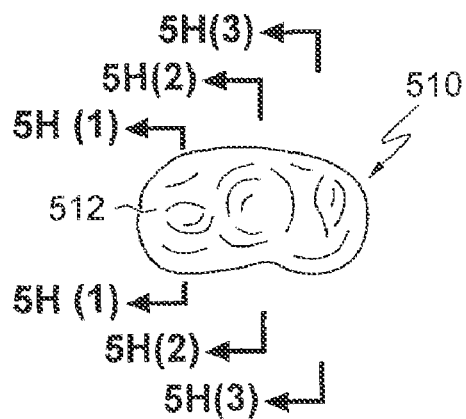

FIGS. 5E-H illustrate the interior, patient specific, piece 510 from a variety of perspectives. FIG. 55E shows a side view of the piece showing the uniform superior surface 514 and the uniform side surfaces 516 along with the irregular inferior surface 516. The inferior surface mates with the irregular surface of the tibia 502. FIG. 5F illustrates a superior view of the interior, patient, specific piece of the mold 510. Optionally having an aperture 530. FIG. 5G illustrates an inferior view of the interior patient specific mold piece 510 further illustrating the irregular surface which includes convex and concave portions to the surface, as necessary to achieve optimal mating with the surface of the tibia. FIG. 5H illustrates cross-sectional views of the interior patient specific mold piece 510. As can be seen in the cross-sections, the surface of the interior surface changes along its length.

As is evident from the views shown in FIGS. 5B and D, the length of the guide plate 526 can be such that it extends along all or part of the tibial plateau, e.g. where the guide plate 526 is asymmetrically positioned as shown in FIG. 5B or symmetrical as in FIG. 3D. If total knee arthroplasty is contemplated, the length of the guide plate 526 typically extends along all of the tibial plateau. If unicompartmental arthroplasty is contemplated, the length of the guide plate typically extends along the length of the compartment that the surgeon will operate on. Similarly, if total knee arthroplasty is contemplated, the length of the molded, interior piece 510 typically extends along all of the tibial plateau; it can include one or both tibial spines. If unicompartmental arthroplasty is contemplated, the length of the molded interior piece typically extends along the length of the compartment that the surgeon will operate on; it can optionally include a tibial spine.

Figure 5I:
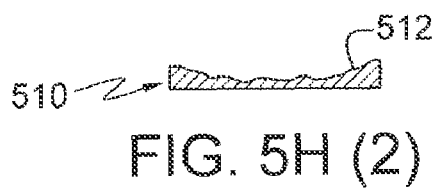
Figure 5I:
Figure 5I:
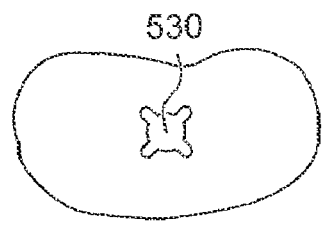

Turning now to FIG. 5I, an alternative embodiment is depicted of the aperture 530. In this embodiment, the aperture features lateral protrusions to accommodate using a reamer or punch to create an opening in the bone that accepts a stem having flanges.

Figure 5J:
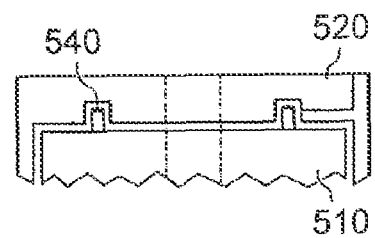
Figure 5K:
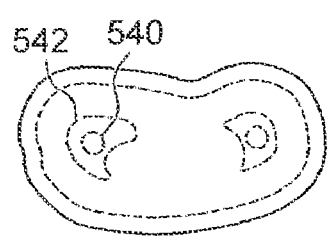
Figure 5L:
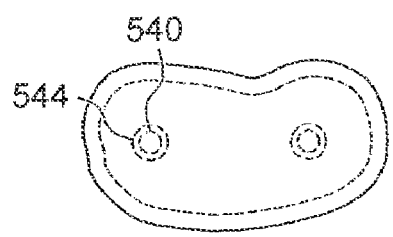

FIGS. 5J and M depict alternative embodiments of the invention designed to control the movement and rotation of the cutting block 520 relative to the mold 510. As shown in FIG. 5J a series of protrusions, illustrated as pegs 540, are provided that extend from the superior surface of the mold. As will be appreciated by those of skill in the art, one or more pegs or protrusions can be used without departing from the scope of the invention. For purposes of illustration, two pegs have been shown in FIG. 5J. Depending on the control desired, the pegs 540 are configured to fit within, for example, a curved slot 542 that enables rotational adjustment as illustrated in FIG. 5K or within a recess 544 that conforms in shape to the peg 540 as shown in FIG. 5L. As will be appreciated by those of skill in the art, the recess 544 can be sized to snugly encompass the peg or can be sized larger than the peg to allow limited lateral and rotational movement.

Figure 5M:
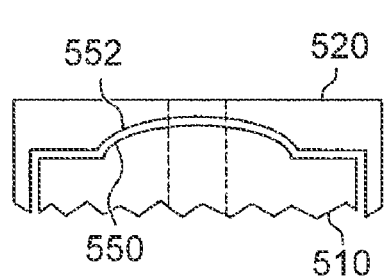

As illustrated in FIG. 5M the surface of the mold 510 can be configured such that the upper surface forms a convex dome 550 that fits within a concave well 552 provided on the interior surface of the cutting block 520. This configuration enables greater rotational movement about the mechanical axis while limiting lateral movement or translation.

Other embodiments and configurations could be used to achieve these results without departing from the scope of the invention.

As will be appreciated by those of skill in the art, more than two pieces can be used, where appropriate, to comprise the system. For example, the patient specific interior piece 510 can be two pieces that are configured to form a single piece when placed on the tibia. Additionally, the exterior piece 520 can be two components. The first component can have, for example, the cutting guide apertures 528. After the resection using the cutting guide aperture 528 is made, the exterior piece 520 can be removed and a secondary exterior piece 520' can be used which does not have the guide plate 526 with the cutting guide apertures 528, but has the aperture 530 which facilitates boring into the tibial surface an aperture to receive a stem of the tibial component of the knee implant. Any of these designs could also feature the surface configurations shown in FIGS. 5J-M, if desired.

Figure 5N:
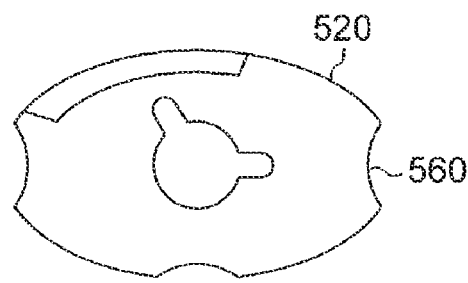

FIG. 5N illustrates an alternative design of the cutting block 520 that provides additional structures 560 to protect, for example, the cruciate ligaments, from being cut during the preparation of the tibial plateau. These additional structures can be in the form of indented guides 560, as shown in FIG. 5N or other suitable structures.

Figure 5O:
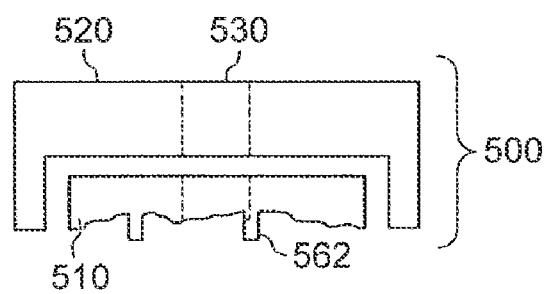

FIG. 5O illustrates a cross-section of a system having anchoring pegs 562 on the surface of the interior piece 510 that anchor the interior piece 510 into the cartilage or meniscal area.

Figure 5P:
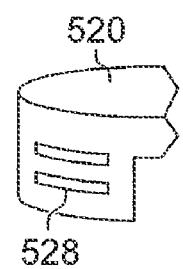
Figure 5Q:
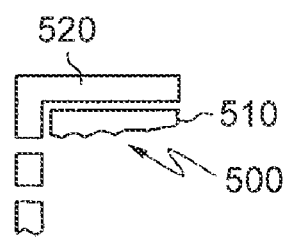

FIGS. 5P AND Q illustrate a device 500 configured to cover half of a tibial plateau such that it is unicompartmental.

Turning now to FIG. 6, a femoral mold system is depicted that facilitates preparing the surface of the femur such that the finally implanted femoral implant will achieve optimal mechanical and anatomical axis alignment.

FIG. 6A illustrates the femur 600 with a first portion 610 of the mold placed thereon. In this depiction, the top surface of the mold 612 is provided with a plurality of apertures. In this instance the apertures consist of a pair of rectangular apertures 614, a pair of square apertures 616, a central bore aperture 618 and a long rectangular aperture 620. The side surface 622 of the first portion 610 also has a rectangular aperture 624. Each of the apertures is larger than the eventual cuts to be made on the femur so that, in the event the material the first portion of the mold is manufactured from a soft material, such as plastic, it will not be inadvertently cut during the joint surface preparation process. Additionally, the shapes can be adjusted, e.g., rectangular shapes made trapezoidal, to give a greater flexibility to the cut length along one area, without increasing flexibility in another area. As will be appreciated by those of skill in the art, other shapes for the apertures, or orifices, can be changed without departing from the scope of the invention.

FIG. 6B illustrates a side view of the first portion 610 from the perspective of the side surface 622 illustrating the aperture 624. As illustrated, the exterior surface 611 has a uniform surface which is flat, or relatively flat configuration while the interior surface 613 has an irregular surface that conforms, or substantially conforms, with the surface of the femur.

FIG. 6C illustrates another side view of the first, patient specific molded, portion 610, more particularly illustrating the irregular surface 613 of the interior. FIG. 6D illustrates the first portion 610 from a top view. The center bore aperture 618 is optionally provided to facilitate positioning the first piece and to prevent central rotation.

FIG. 6D illustrates a top view of the first portion 610. The bottom of the illustration corresponds to an anterior location relative to the knee joint. From the top view, each of the apertures is illustrated as described above. As will be appreciated by those of skill in the art, the apertures can be shaped differently without departing from the scope of the invention.

Turning now to FIG. 6E, the femur 600 with a first portion 610 of the cutting block placed on the femur and a second, exterior, portion 640 placed over the first portion 610 is illustrated. The second, exterior, portion 640 features a series of rectangular grooves (642-650) that facilitate inserting a saw blade therethrough to make the cuts necessary to achieve the femur shape illustrated in FIG. 1E. These grooves can enable the blade to access at a 90° angle to the surface of the exterior portion, or, for example, at a 45° angle. Other angles are also possible without departing from the scope of the invention.

As shown by the dashed lines, the grooves (642-650) of the second portion 640, overlay the apertures of the first layer.

FIG. 6F illustrates a side view of the second, exterior, cutting block portion 640. From the side view a single aperture 650 is provided to access the femur cut. FIG. 6G is another side view of the second, exterior, portion 640 showing the location and relative angles of the rectangular grooves. As evidenced from this view, the orientation of the grooves 642, 648 and 650 is perpendicular to at least one surface of the second, exterior, portion 640. The orientation of the grooves 644, 646 is at an angle that is not perpendicular to at least one surface of the second, exterior portion 640. These grooves (644, 646) facilitate making the angled chamfer cuts to the femur. FIG. 6H is a top view of the second, exterior portion 640. As will be appreciated by those of skill in the art, the location and orientation of the grooves will change depending upon the design of the femoral implant and the shape required of the femur to communicate with the implant.

Figure 6J:
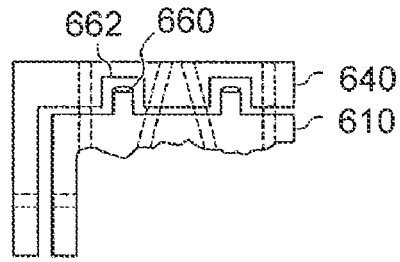
FIGS. 6A-O illustrate femur cutting blocks and molds used to create a surface for receiving the femoral portion of a knee implant.

FIG. 6I illustrates a spacer 601 for use between the first portion 610 and the second portion 640. The spacer 601 raises the second portion relative to the first portion, thus raising the area at which the cut through groove 624 is made relative to the surface of the femur. As will be appreciated by those of skill in the art, more than one spacer can be employed without departing from the scope of the invention. Spacers can also be used for making the tibial cuts. Optional grooves or channels 603 can be provided to accommodate, for example, pins 660 shown in FIG. 6J.

Similar to the designs discussed above with respect to FIG. 5, alternative designs can be used to control the movement and rotation of the cutting block 640 relative to the mold 610. As shown in FIG. 6J a series of protrusions, illustrated as pegs 660, are provided that extend from the superior surface of the mold. These pegs or protrusions can be telescoping to facilitate the use of molds if necessary. As will be appreciated by those of skill in the art, one or more pegs or protrusions can be used without departing from the scope of the invention. For purposes of illustration, two pegs have been shown in FIG. 66J. Depending on the control desired, the pegs 660 are configured to fit within, for example, a curved slot that enables rotational adjustment similar to the slots illustrated in FIG. 5K or within a recess that conforms in shape to the peg, similar to that shown in FIG. 5L and described with respect to the tibial cutting system. As will be appreciated by those of skill in the art, the recess 662 can be sized to snugly encompass the peg or can be sized larger than the peg to allow limited lateral and rotational movement.

Figure 6K:
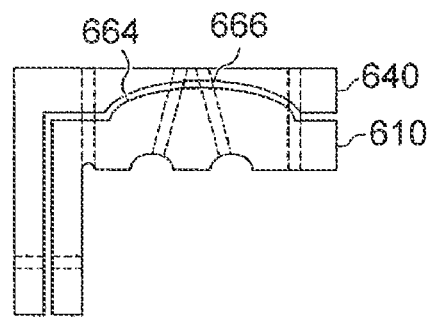
Figure 6L:
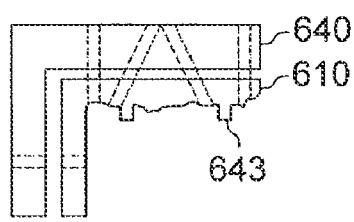
Figure 6M:
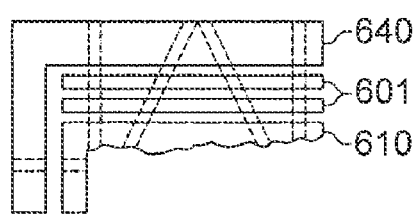

As illustrated in FIG. 6K the surface of the mold 610 can be configured such that the upper surface forms a convex dome 664 that fits within a concave well 666 provided on the interior surface of the cutting block 640. This configuration enables greater rotational movement about the mechanical axis while limiting lateral movement or translation.

In installing an implant, first the tibial surface is cut using a tibial block, such as those shown in FIG. 6. The patient specific mold is placed on the femur. The knee is then placed in extension and spacers 670, such as those shown in FIG. 6I, or shims are used, if required, until the joint optimal function is achieved in both extension and flexion. The spacers, or shims, are typically of an incremental size, e.g., 5 mm thick to provide increasing distance as the leg is placed in extension and flexion. A tensiometer can be used to assist in this determination or can be incorporated into the mold or spacers in order to provide optimal results. The design of tensiometers are known in the art and are not included herein to avoid obscuring the invention. Suitable designs include, for example, those described in U.S. Pat. No. 5,630,820 to Todd issued May 20, 1997.

Figure 6N:
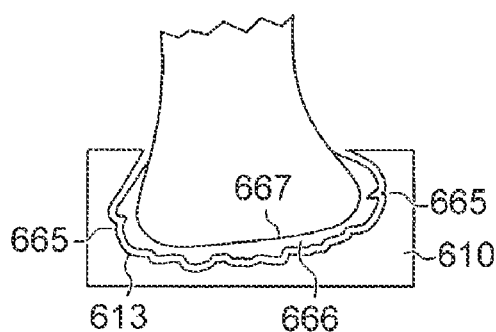
Figure 6O:
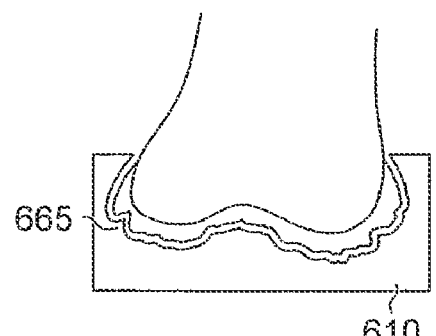

As illustrated in FIGS. 6N (sagittal view) and 6M (coronal view), the interior surface 613 of the mold 610 can include small teeth 665 or extensions that can help stabilize the mold against the cartilage 666 or subchondral bone 667.

Turning now to FIG. 7, a variety of illustrations are provided showing a patellar cutting block and mold system. FIGS. 7A-C illustrates the patellar cutting block 700 in conjunction with a patella 702 that has not been resected. In this depiction, the cutting block 700 can consist of only one piece or a plurality of pieces, if desired. The inner surface 703 is patient specific and designed to mate, or substantially mate, with the existing geography of the patient's patella 702. Small openings are present 707 to accept the saw. The mold or block can have only one or multiple openings. The openings can be larger than the saw in order to allow for some rotation or other fine adjustments. FIG. 7A is a view in the sagittal plane A. The quadriceps tendon 704 and patellar tendon 705 are shown.

Figure 7A:
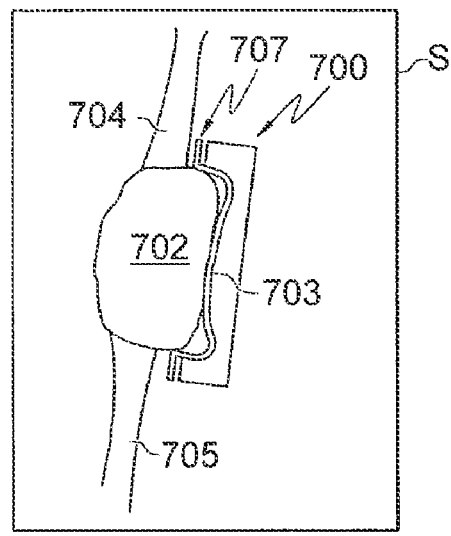
Figure 7B:
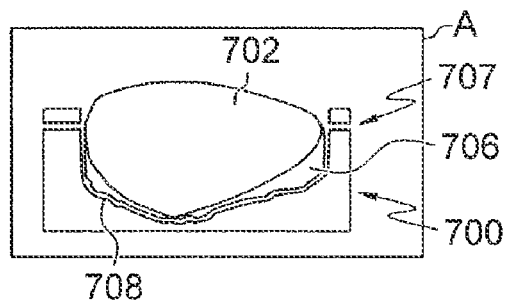
Figure 7C:
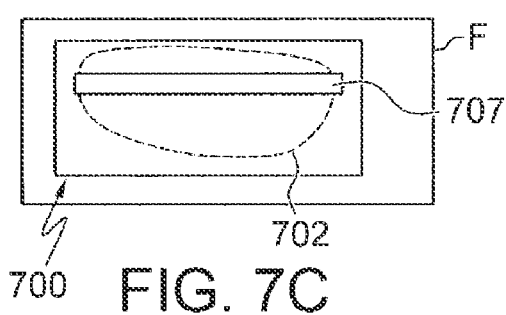

FIG. 7B is a view in the axial plane A. The cartilage 706 is shown. The mold can be molded to the cartilage or the subchondral bone or combinations thereof. FIG. 7C is a frontal view F of the mold demonstrating the opening for the saw 707. The dashed line indicates the relative position of the patella 702.

Figure 7D:
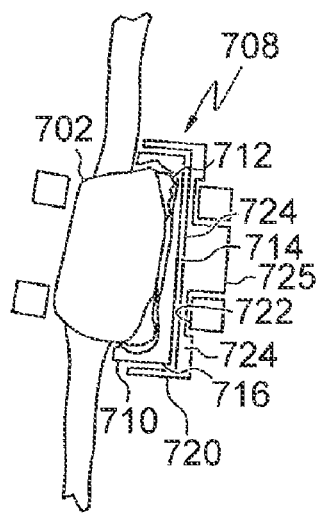

FIGS. 7D (sagittal view) and E (axial view) illustrate a patellar cutting block 708 in conjunction with a patella 702 that has not been resected. In this depiction, the cutting block 708 consists of at least two pieces. The first piece is a patient specific interior piece 710 or mold that is designed on its inferior surface 712 to mate, or substantially mate, with the existing geography of the patient's patella 702. The posterior surface 714 and side surfaces 716 of the first piece 710 are configured to mate within the interior of an exterior piece 720. The reusable exterior piece 720 fits over the interior piece 710 and holds it onto the patella. The reusable exterior piece has an interior surface 724 that mates with the first piece 710. The reusable exterior piece 720 includes cutting guides 707, to assist the surgeon in performing the patellar surface cut. A plurality of cutting guides can be provided to provide the surgeon a variety of locations to choose from in making the patellar cut. If necessary, additional spacers can be provided that fit between the first patient configured, or molded, piece 710 and the second reusable exterior piece, or cutting block, 720.

The second reusable exterior piece, or cutting block, 720, can have grooves 722 and extensions 725 designed to mate with surgical instruments such as a patellar clamp 726. The patellar clamp 726 can have ring shaped graspers 728 and locking mechanisms, for example ratchet-like 730. The opening 732 in the grasper fits onto the extension 725 of the second reusable exterior piece 720. Portions of a first portion of the handle of the grasper can be at an oblique angle 734 relative to the second portion of the handle, or curved (not shown), in order to facilitate insertion. Typically the portion of the grasper that will be facing towards the intra-articular side will have an oblique or curved shaped thereby allowing a slightly smaller incision.

The variable nature of the interior piece facilitates obtaining the most accurate cut despite the level of disease of the joint because it positions the exterior piece 720 in the desired plane. Either the interior piece 710 or the exterior piece 720 can be formed out of any of the materials discussed above in Section II, or any other suitable material. Additionally, a person of skill in the art will appreciate that the invention is not limited to the two piece configuration described herein. The reusable exterior piece 720 and the patient specific interior piece 710 can be a single piece that is either patient specific (where manufacturing costs of materials support such a product) or is reusable based on a library of substantially defect conforming shapes developed in response to known or common tibial surface sizes and defects.

The interior piece 710 is typically molded to the patella including the subchondral bone and/or the cartilage.

From this determination, an understanding of the amount of space needed to balance the knee is determined and an appropriate number of spacers is then used in conjunction with the cutting block and mold to achieve the cutting surfaces and to prevent removal of too much bone. Where the cutting block has a thickness of, for example, 10 mm, and each spacer has a thickness of 5 mm, in preparing the knee for cuts, two of the spacers would be removed when applying the cutting block to achieve the cutting planes identified as optimal during flexion and extension. Similar results can be achieved with ratchet or jack like designs interposed between the mold and the cut guide.

Turning now to FIG. 8, a variety of views showing sample mold and cutting block systems for use in the hip joint are shown. FIG. 8A illustrates femur 810 with a mold and cutting block system 820 placed to provide a cutting plane 830 across the femoral neck 812 to facilitate removal of the head 814 of the femur and creation of a surface 816 for the hip ball prosthesis.

Figure 8A:
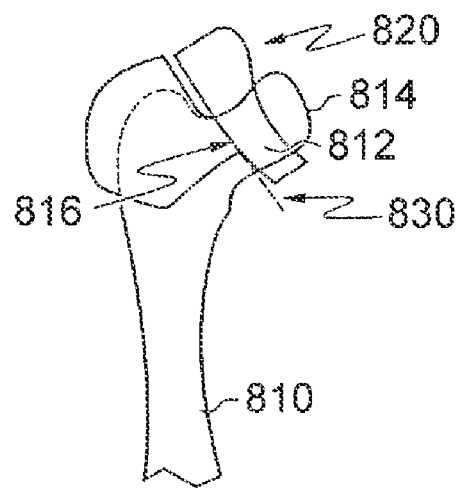
FIG. 8A-H illustrate femoral head cutting blocks and molds used to create a surface for receiving the femoral portion of a knee implant.
Figure 8B:
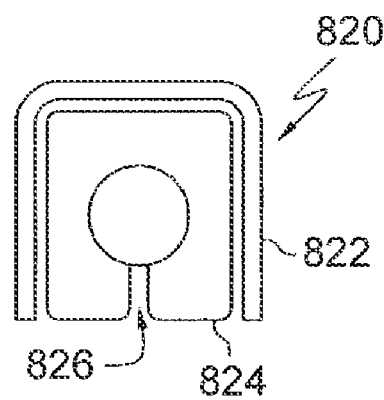

FIG. 8B illustrates a top view of the cutting block system 820. The cutting block system 820 includes an interior, patient specific, molded section 824 and an exterior cutting block surface 822. The interior, patient specific, molded section 824 can include a canal 826 to facilitate placing the interior section 824 over the neck of the femur. As will be appreciated by those of skill in the art, the width of the canal will vary depending upon the rigidity of the material used to make the interior molded section. The exterior cutting block surface 822 is configured to fit snugly around the interior section. Additional structures can be provided, similar to those described above with respect to the knee cutting block system, that control movement of the exterior cutting block 824 relative to interior mold section 822, as will be appreciated by those of skill in the art. Where the interior section 824 encompasses all or part of the femoral neck, the cutting block system can be configured such that it aids in removal of the femoral head once the cut has been made by, for example, providing a handle 801.

Figure 8C:
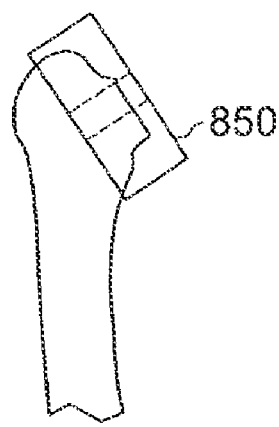
Figure 8D:
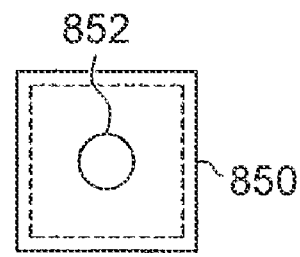
Figure 8E:
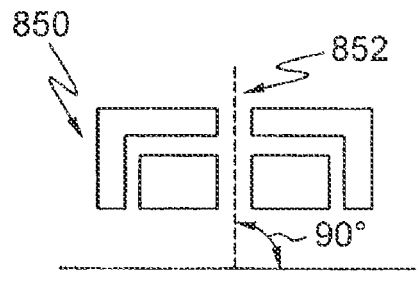
Figure 8F:
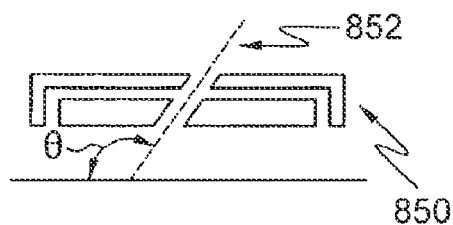
Figure 8G:
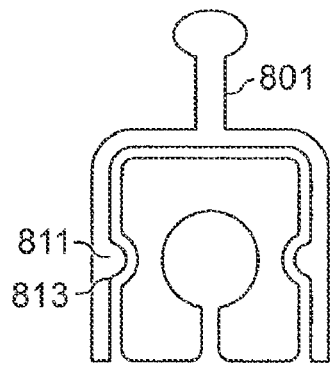
Figure 8H:
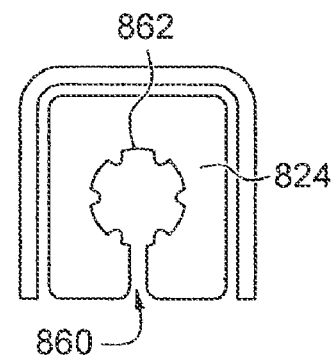

FIG. 8C illustrates a second cutting block system 850 that can be placed over the cut femur to provide a guide for reaming after the femoral head has been removed using the cutting block shown in FIG. 8A. FIG. 8D is a top view of the cutting block shown in FIG. 8C. As will be appreciated by those of skill in the art, the cutting block shown in FIG. 8C-D, can be one or more pieces. As shown in FIG. 8E, the aperture 852 can be configured such that it enables the reaming for the post of the implant to be at a 90° angle relative to the surface of femur. Alternatively, as shown in FIG. 8F, the aperture 852 can be configured to provide an angle other than 90° for reaming, if desired.

Figure 9A:
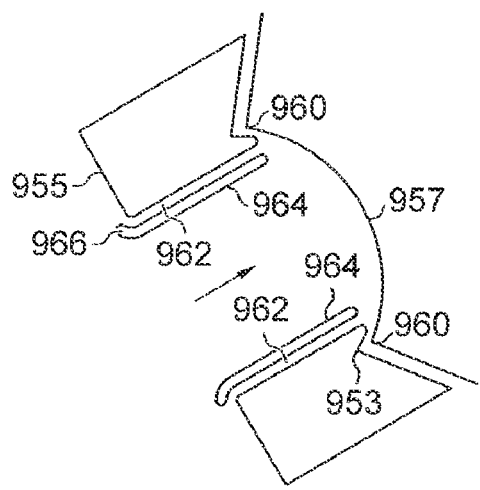
FIG. 9A-D illustrate acetabulum cutting blocks and molds used to create a surface for a hip implant.

FIGS. 9A (sagittal view) and 9B (frontal view, down onto mold) illustrates a mold system 955 for the acetabulum 957. The mold can have grooves 959 that stabilize it against the acetabular rim 960. Surgical instruments, e.g. reamers, can be passed through an opening in the mold 956. The side wall of the opening 962 can guide the direction of the reamer or other surgical instruments. Metal sleeves 964 can be inserted into the side wall 962 thereby protecting the side wall of the mold from damage. The metal sleeves 964 can have lips 966 or overhanging edges that secure the sleeve against the mold and help avoid movement of the sleeve against the articular surface.

Figure 9B:
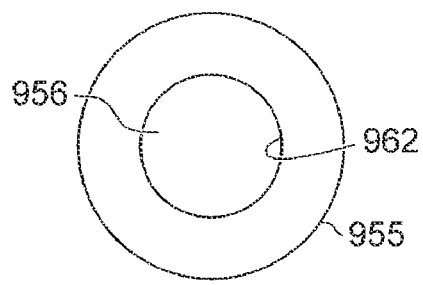
Figure 9C:
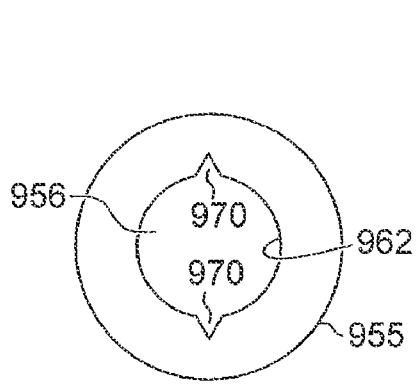

FIG. 9C is a frontal view of the same mold system shown in FIGS. 9A and 9B. A groove 970 has been added at the 6 and 12 o'clock positions. The groove can be used for accurate positioning or placement of surgical instruments. Moreover, the groove can be useful for accurate placement of the acetabular component without rotational error. Someone skilled in the art will recognize that more than one groove or internal guide can be used in order to not only reduce rotational error but also error related to tilting of the implant. As seen FIG. 9D, the implant 975 can have little extensions 977 matching the grooves thereby guiding the implant placement. The extensions 977 can be a permanent part of the implant design or they can be detachable. Note metal rim 979 and inner polyethylene cup 980 of the acetabular component.

Figure 9D:
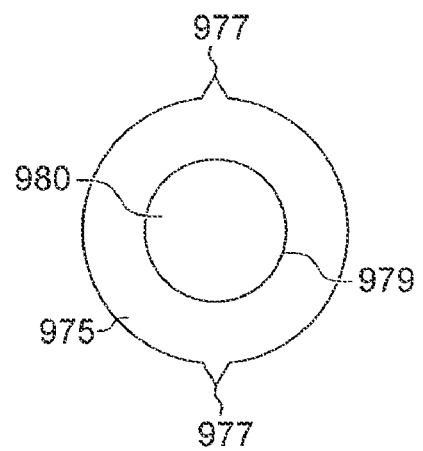

FIG. 9D illustrates a cross-section of a system where the interior surface 960 of the molded section 924 has teeth 962 or grooves to facilitate grasping the neck of the femur.

After identification of the cartilage defect and marking of the skin surface using the proprietary U-shaped cartilage defect locator device as described herein, a 3 cm incision is placed and the tissue retractors are inserted. The cartilage defect is visualized.

A first Lucite block matching the 3D surface of the femoral condyle is placed over the cartilage defect. The central portion of the Lucite block contains a drill hole with an inner diameter of, for example, 1.5 cm, corresponding to the diameter of the base plate of the implant. A standard surgical drill with a drill guide for depth control is inserted through the Lucite block, and the recipient site is prepared for the base component of the implant. The drill and the Lucite block are then removed.

A second Lucite block of identical outer dimensions is then placed over the implant recipient site. The second Lucite block has a rounded, cylindrical extension matching the size of the first drill hole (and matching the shape of the base component of the implant), with a diameter 0.1 mm smaller than the first drill hole and 0.2 mm smaller than that of the base of the implant. The cylindrical extension is placed inside the first drill hole.

The second Lucite block contains a drill hole extending from the external surface of the block to the cylindrical extension. The inner diameter of the second drill hole matches the diameter of the distal portion of the fin-shaped stabilizer strut of the implant, e.g. 3 mm. A drill, e.g. with 3 mm diameter, with a drill guide for depth control is inserted into the second hole and the recipient site is prepared for the stabilizer strut with a four fin and step design. The drill and the Lucite block are then removed.

A plastic model/trial implant matching the 3-D shape of the final implant with a diameter of the base component of 0.2 mm less than that of the final implant and a cylindrical rather than tapered strut stabilizer with a diameter of 0.1 mm less than the distal portion of the final implant is then placed inside the cartilage defect. The plastic model/trial implant is used to confirm alignment of the implant surface with the surrounding cartilage. The surgeon then performs final adjustments.

The implant is subsequently placed inside the recipient site. The anterior fin of the implant is marked with red color and labeled "A." The posterior fin is marked green with a label "P" and the medial fin is color coded yellow with a label "M." The Lucite block is then placed over the implant. A plastic hammer is utilized to advance the implant slowly into the recipient site. A press fit is achieved with help of the tapered and four fin design of the strut, as well as the slightly greater diameter (0.1 mm) of the base component relative to the drill hole. The Lucite block is removed. The tissue retractors are then removed. Standard surgical technique is used to close the 3 cm incision. The same procedure described above for the medial femoral condyle can also be applied to the lateral femoral condyle, the medial tibial plateau, the lateral tibial plateau and the patella. Immediate stabilization of the device can be achieved by combining it with bone cement if desired.

Figure 10A:
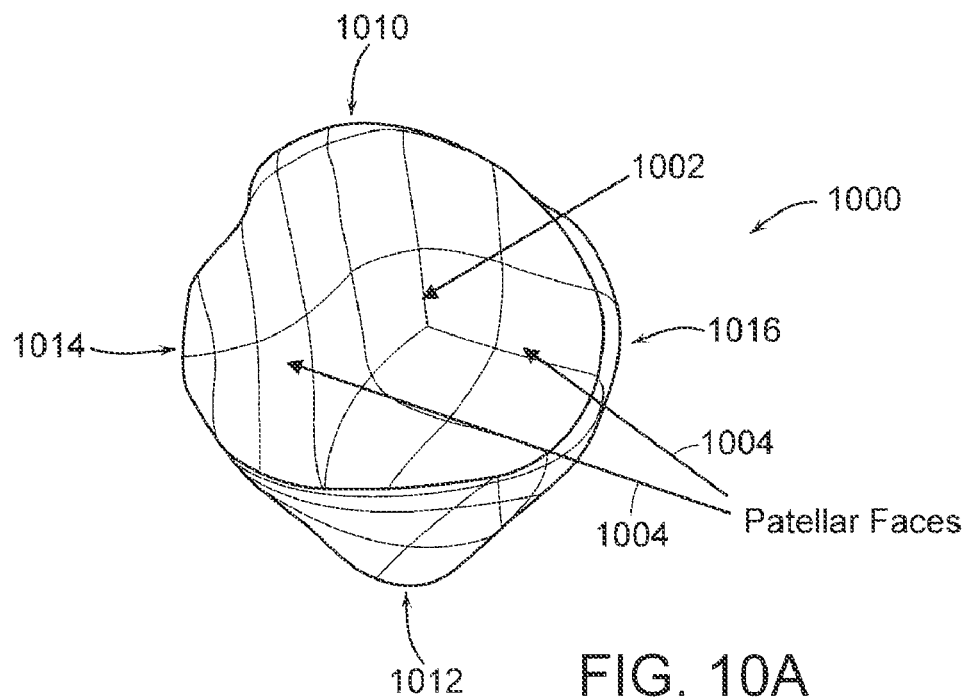
FIG. 10A illustrates a patella modeled from CT data.

FIG. 10A illustrates a patella 1000 having a patellar ridge 1002, patellar facets 1004, 1004. Also depicted are the superior 1010, inferior 1012, lateral 1014, and medial 1016 surfaces.

Figure 10B:
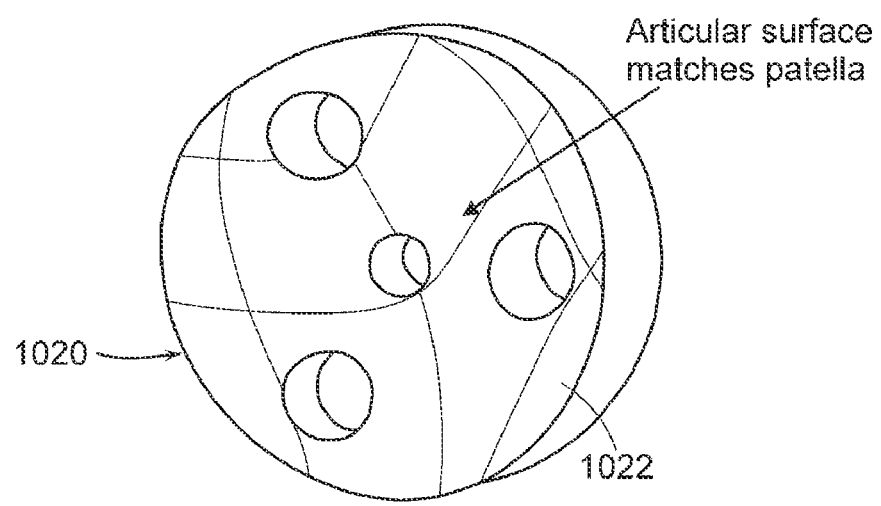
FIGS. 10B-D illustrate a mold guide, and then the mold guide placed on an articular surface of the patella.

FIG. 10B illustrates a mold drill guide 1020 from the perspective of the tibial matching surface 1022. The mold drill guide 1020 is configured so that it is substantially a round cylinder. However, other shapes can be employed without departing from the scope of the invention. Such shapes can be strictly geometrical, e.g. ovoid, or non-geometrical.

The tibial matching surface 1022 has an articular surfaces that matches, or closely conforms, to, the surface of the patella. The design is proposed such that the guide is molded to precisely fit the anatomy of the articular surface of the patella for each patient, thus providing precise location of the patella planning needed. As will be appreciated by those of skill in the art, while an exact or precise fit is desired, deviations from a precise fit can occur without departing from the scope of the invention. Thus, it is anticipated that a certain amount of error in the design can be tolerated.

Figure 10C:
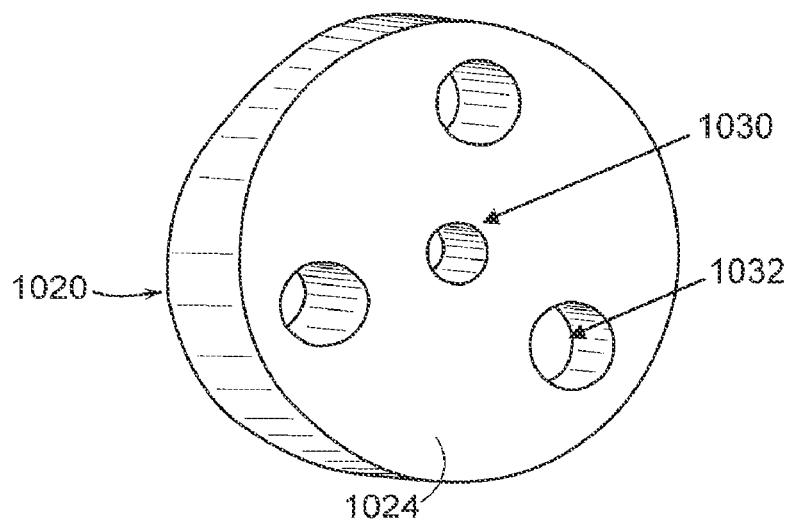

FIG. 10C illustrates the guide 1020 from the opposite perspective. The planar guide surface 1024 is depicted as flat, or substantially flat. However, as will be appreciated by those of skill in the art, other surface configurations can be employed without departing from the scope of the invention. Both FIGS. 10A and B depict apertures 1030, 1032. A central aperture 1030 is provided that accommodates, for example, a ⅛ drill bit. The central aperture 1030 can be located such that it is centered within the guide, off-centered, or slightly off-centered, without departing from the scope of the invention. An off-center or slightly off-center configure could be used with the round cylindrical configuration, but could also be used with the other configurations as well. One or more additional apertures 1032 can be provided to enable peg holes to be drilled. The apertures 1032 can be configured to have a larger diameter as the first aperture 1030, a smaller diameter, or an identical diameter.

Figure 10D:
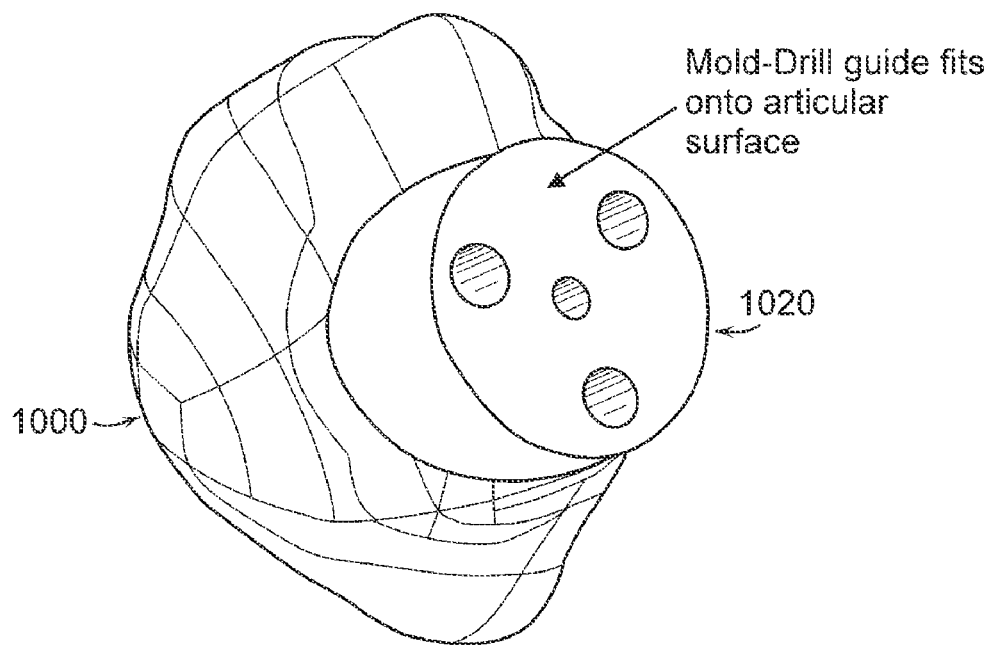
Figure 10E:
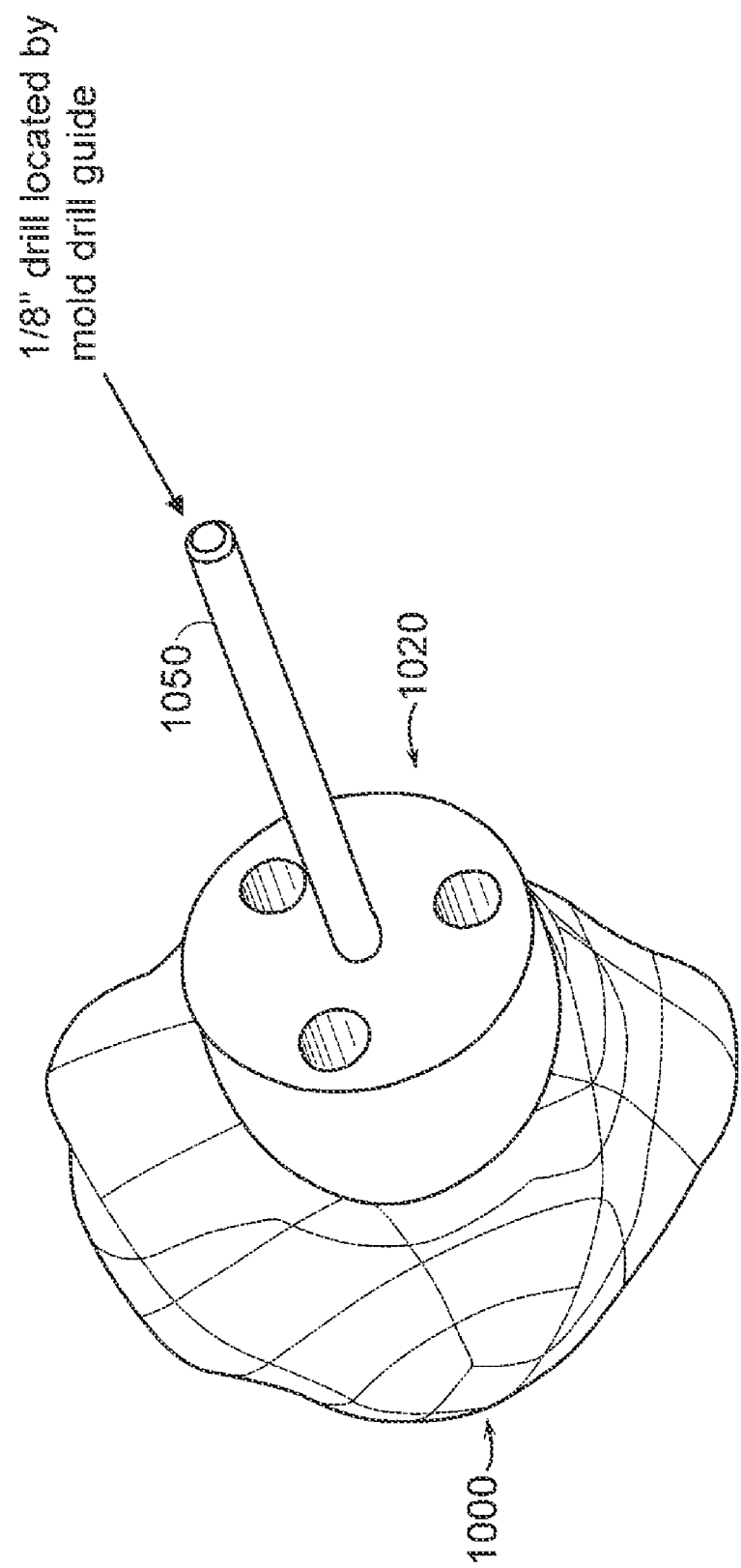
FIG. 10E illustrates a drill placed into a patella through mold drill guide.
Figure 10F:
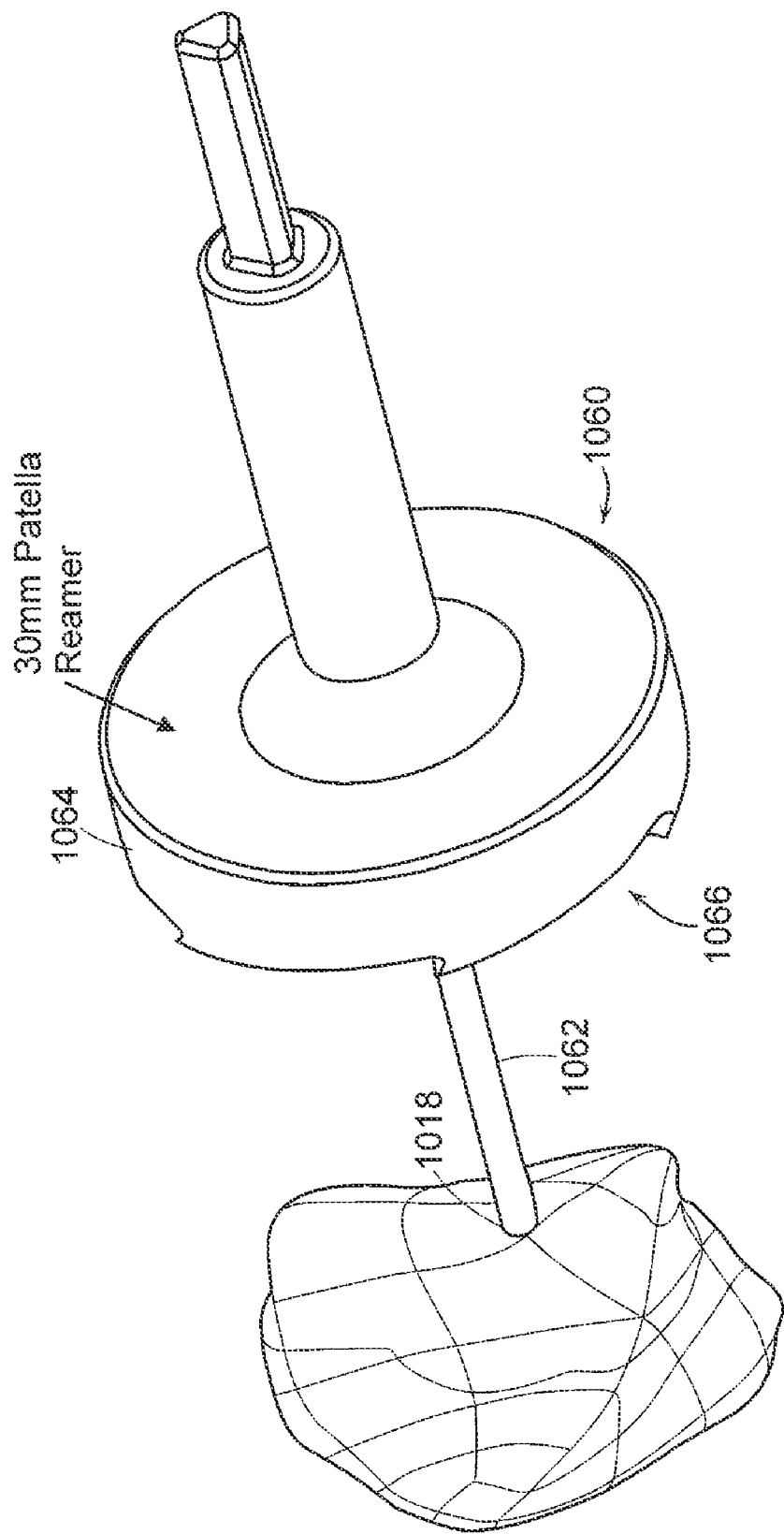
FIG. 10F illustrates a reamer used to prepare the patella.

As shown in FIG. 10D the mold drill guide is fitted onto the articular surface of the patella. Because the articular facing surface (shown in FIG. 10A) is configured to match or substantially match the articular surface of the patella, the drill guide mates with the patellar surface to enable the drill holes to line-up in the desired place for the implant. FIG. 10E illustrates the mold drill guide fitted onto the articular surface of the patella with a ⅛" drill 1050 positioned within the central aperture 1030.

Once a central aperture 1018 has been formed into the patella, a patella reamer 1060 is used to resurface the patella 1000. The reamer 1060 has a guide 1062, which fits within the aperture 1018, and a reamer 1064 having a planing surface or blade surface 1066.

Figure 11A:
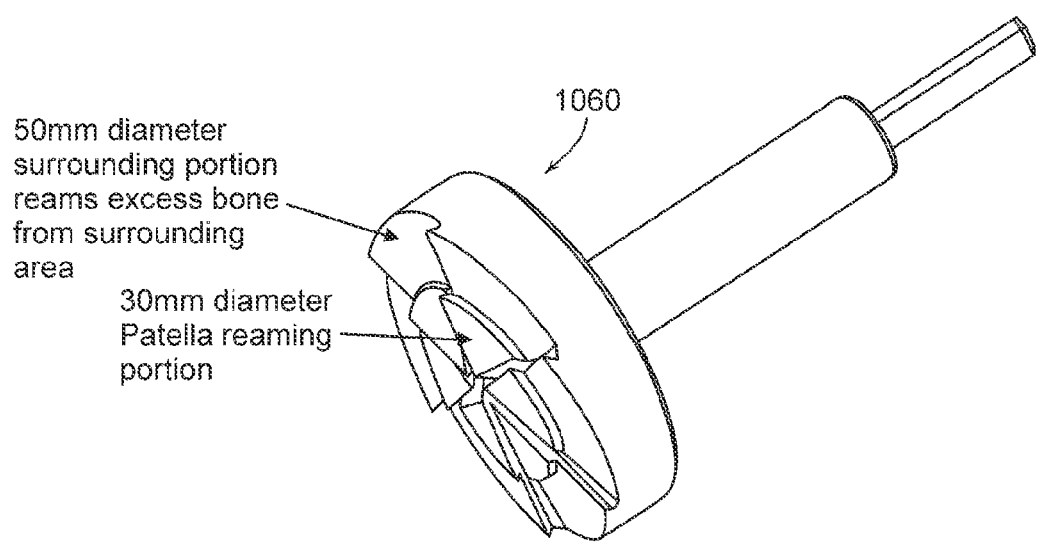
FIG. 11A illustrates a reamer made for each patella size.
Figure 11B:
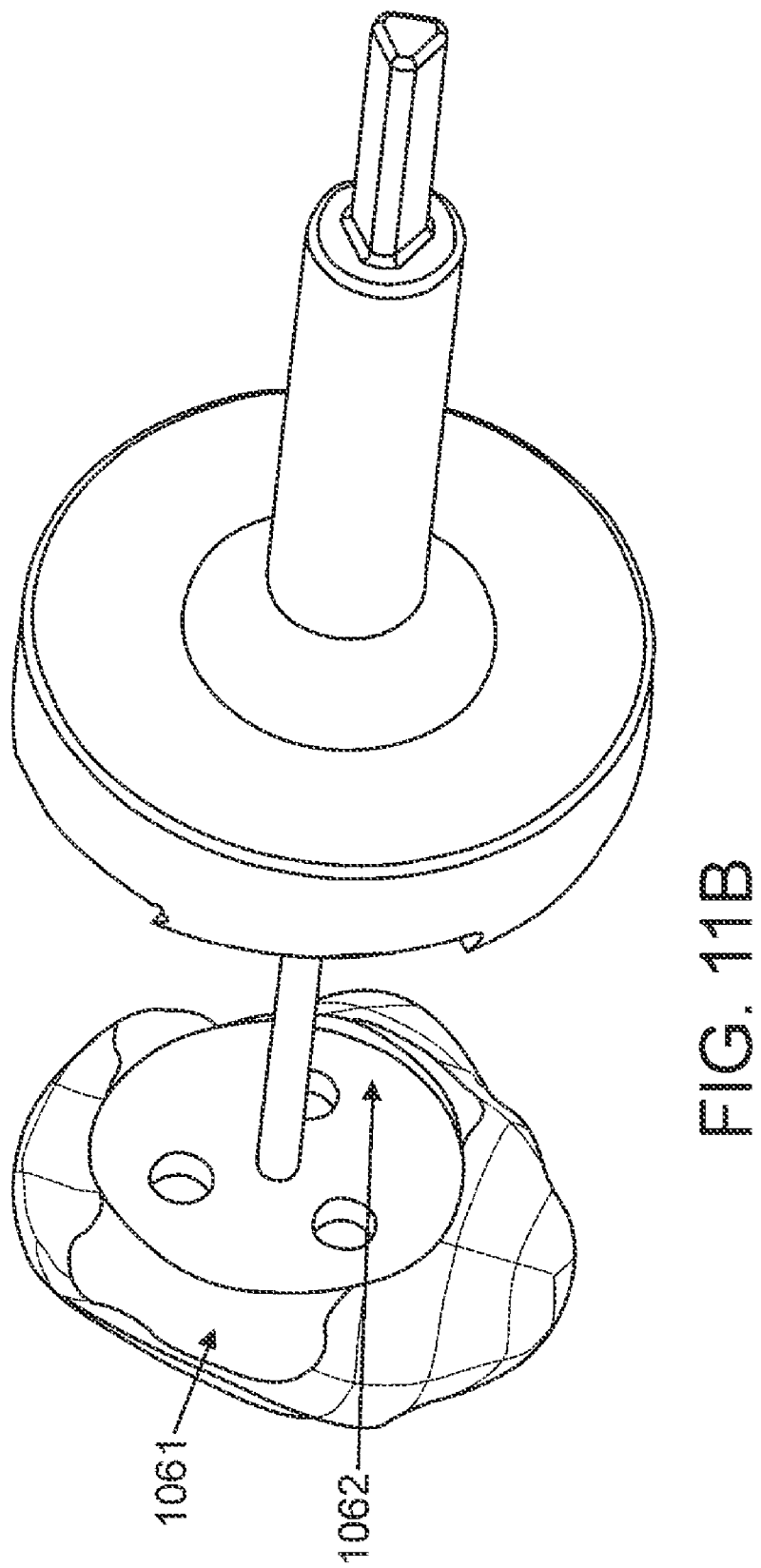
FIG. 11B illustrates a reamed patella ready for patella implantation.

Turning to FIG. 11A the reamer 1060 is shown. The planning surface 1066 has is configured to provide dual planing surfaces in order to recess the patella and clear surrounding bone. Providing dual planing surfaces helps to insure polymetal articulation only. FIG. 11B illustrates the reamer relative to a patella. An area is prepared 1062 for a 30 mm patella insert, and a surrounding area 1061 is reamed.

Figure 12A:
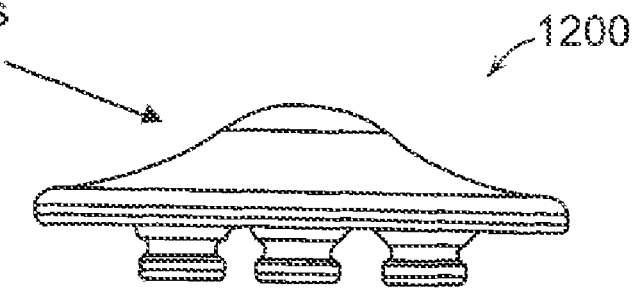
FIG. 12A-F illustrate a recessed patella implanted on a patella.
Figure 12B:
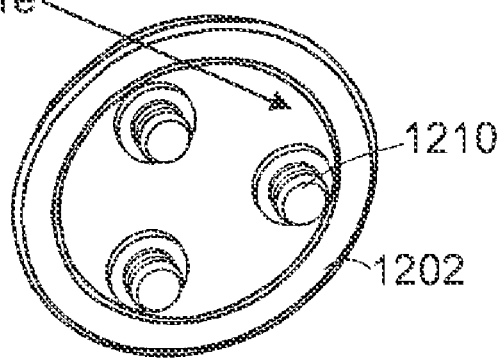
Figure 12C:
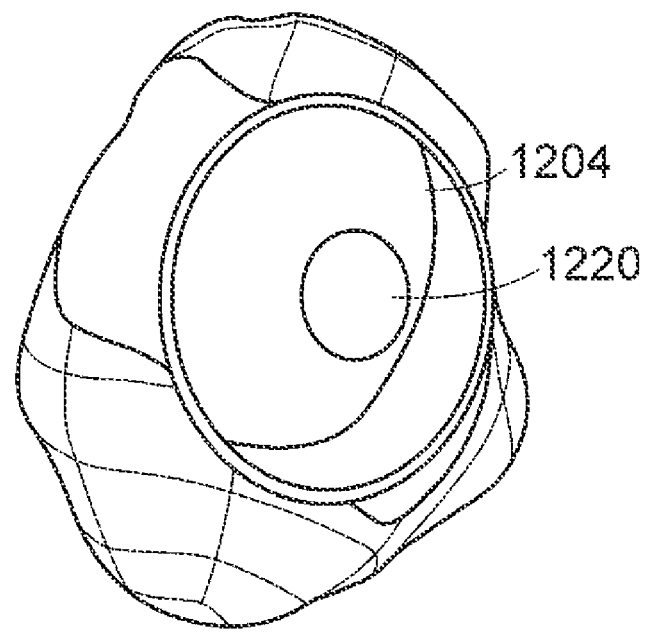
Figure 12D:
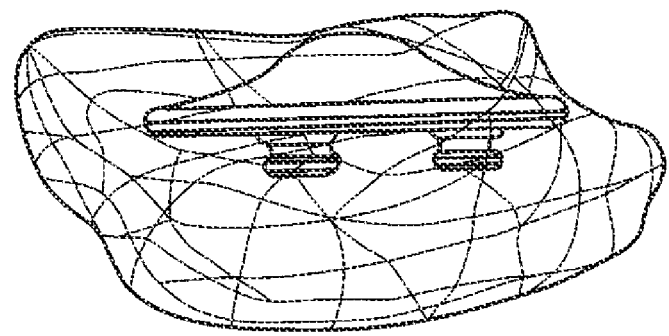
Figure 12E:
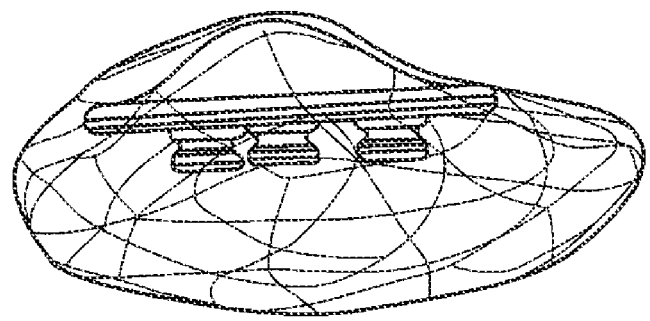
Figure 12F:
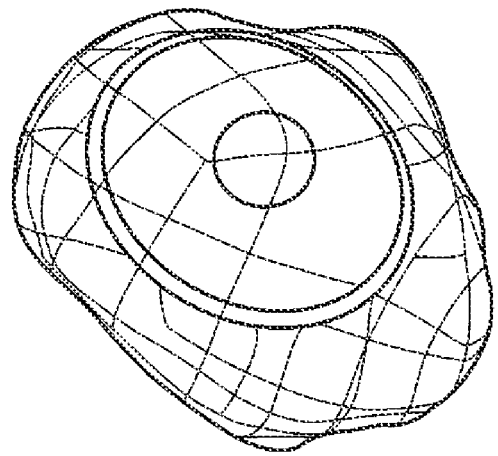

FIG. 12A illustrates a patella implant 1200. The inferior surface of the implant 1200, has one or more pegs 1210. In this instance, the inferior surface 1202 is depicted with three pegs 1210. The implant 1200 is positioned on a patella as shown in FIG. 12C such that a protuberance 1220 on the superior surface 1204 of the implant is positioned approximately at the apex of the natural patella. FIGS. 12D-F illustrate the implant superimposed within a patella, more clearly showing the protuberance corresponding to the apex of the natural patella.

Also described herein are kits comprising one or more of the methods, systems and/or compositions described herein. In particular, a kit can include one or more of the following: instructions (methods) of obtaining electronic images; systems or instructions for evaluating electronic images; one or more computer means capable of analyzing or processing the electronic images; and/or one or more surgical tools for implanting an articular repair system. The kits can include other materials, for example, instructions, reagents, containers and/or imaging aids (e.g., films, holders, digitizers, etc.).

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims equivalents thereof.

What is claimed:

1. A method of making a surgical tool, the method comprising:
   obtaining images data associated with at least a portion of a joint; and
   deriving a substantially uncut cartilage surface associated with the joint from the image data; and
   providing a surgical tool that includes a contact surface for engaging the substantially uncut cartilage surface associated with the joint, the surgical tool further including at least one guide for directing movement of a surgical instrument in preparing an implant site, wherein providing the surgical tool includes:
   shaping the contact surface based on the derived cartilage surface such that the contact surface conforms to and is substantially a negative of the derived cartilage surface; and
   determining position, shape and/or orientation of the at least one guide from the image data, so that changes induced on the implant site by the surgical instrument ensures a desired orientation of an implant.

2. The method according to claim 1, wherein providing the surgical tool includes providing a second component for engaging a first component, the first component including said contact surface.

3. The method according to claim 2, wherein said second component includes one or more of the at least one guide.

4. The method according to claim 2, wherein the surgical tool further includes an adjustment mechanism for adjusting the position and/or the orientation of at least one guide on the first and/or second component relative to the contact surface to allow for ligament balancing.

5. The method according to claim 4, wherein the adjustment mechanism includes at least one of a spacer, a shim, a ratchet, a hinge, a tensiometer and a jack.

6. The method according to claim 2, wherein a surface of the first component that engages with a surface of the second component is configured to prevent at least one movement selected from the group consisting of axial, lateral and rotational.

7. The method according to claim 2 wherein a surface of the second component that engages the first component is at least one of convex or concave.

8. The method according to claim 2 wherein a surface of the first component that engages the second component is at least one of convex or concave.

9. The method according to claim 2, wherein a surface of one of the first component and the second component has an aperture for receiving at least one of a pin, post and peg located on a surface of the other of the first component and the second component.

10. The method according to claim 9 wherein the aperture forms a groove providing rotational movement.

11. The method of claim 1, further comprising:
    engaging the contact surface of the surgical tool with the cartilage surface associated with the joint; and
    directing movement of the surgical instrument in preparing an implant site using the at least one guide.

12. The method according to claim 1, wherein the at least one guide is one of a guide aperture, a reaming aperture, a drill aperture and a cut plane.

13. The method according to claim 1, wherein the shape of the at least one guide includes at least one guide element for ensuring the desired orientation of the implant.

14. The method according to claim 13, wherein the at least one guide element is a groove.

15. The method according to claim 1, wherein the shape of the at least one guide directs the surgical instrument in making a bone cut that mates with a shaped surface on the implant to ensure the desired implant orientation.

16. The method according to claim 1, wherein the guide has a keyed shape that corresponds to a keyed shape of the implant, such that changes induced on the implant site by the surgical instrument ensures that the implant interlocks with the implant site in the predetermined implant orientation.

17. The method according to claim 1, wherein obtaining the images data includes performing cross-sectional imaging.

18. The method according to claim 1, wherein obtaining the image data includes performing at least one of an MRI, a CT, an optical imaging modality, an x-ray imaging modality and an ultrasound.

19. The method according to claim 1, wherein obtaining the image data includes performing a spiral CT scan.

20. The method according to claim 1, wherein obtaining the image data includes scanning more than one joint.

21. The method according to claim 1, wherein determining shape and/or orientation of the at least one guide includes configuring a first guide to be at an angle to a second guide.

22. The method according to claim 1, wherein providing the surgical tool includes providing a stabilizer that engages the joint.

23. The method according to claim 22, wherein the stabilizer is selected from the group consisting of pin, peg, post, and nub.

24. The method according to claim 1 wherein providing the surgical tool includes further providing at least one of a spacer, a shim, a ratchet, a hinge, a tensiometer and a jack.

25. The method according to claim 1, further comprising using the surgical tool with at least one of hip, knee, ankle, shoulder, elbow, spine and wrist joint.

26. The method according to claim 1, further comprising determining, from said image data, the desired orientation of the implant in relation to at least one of an anatomic landmark, an anatomic axis, and a biomechanical axis associated with the joint.

27. The method according to claim 1, wherein the guide includes a metal covering.

28. The method according to claim 1, wherein the guide directs the surgical instrument in making a bone cut at a predetermined distance from a cartilage surface.

29. The method according to claim 1, wherein the surgical tool farther includes an adjustment mechanism for adjusting the position and/or orientation of the at least one guide relative to the contact surface to allow for ligament balancing.

30. The tool according to claim 29, wherein the adjustment mechanism includes at least one of a spacer, a shim, a ratchet, a hinge, a tensiometer and a jack.

31. The method according to claim 1, wherein providing the surgical tool includes providing at least one surface adapted to rest on bone.

32. The method according to claim 31, wherein the at least one surface adapted to rest on bone is a mirror image of the bone.

33. The method according to claim 1, wherein providing the surgical tool includes providing at least one surface adapted to rest on subchondral bone.

34. The method according to claim 33, wherein the at least one surface adapted to rest on subchondral bone is a mirror image of the subchondral bone.

35. The method according to claim 1, wherein providing the surgical tool includes providing a first component and a second component, the first component including said contact surface, the second component adjustable in position for ligament balancing.

36. The method according to claim 1, wherein the cartilage surface includes diseased cartilage.

37. The method according to claim 1, further comprising using the image data to obtain one of a position, a shape and an orientation of the implant.

38. The method according to claim 1, further comprising evaluating fit between the implant and the implant site using the image data.

39. The method according to claim 38, wherein the image data is three dimensional image data.

40. The method according to claim 11, further comprising determining one of a mechanical axis and an anatomical axis associated with a tibia from the image data, wherein directing movement of the surgical instrument includes cutting the tibia at a predetermined slope in the sagittal plane relative to the one of the mechanical axis and the anatomical axis.

41. The method according to claim 40, wherein said slope is between 0 and 7 degrees from the perpendicular of the one of the mechanical axis and the anatomical axis.

42. The method according to claim 40, wherein the slope matches the normal slope of the tibia.

43. The method according to claim 40, further comprising resting at least a portion of the tool on the tibia prior to directing movement of the surgical instrument.

44. The method according to claim 1, further comprising at least one of generating and selecting an implant based, at least in part, on said image data.

45. The method according to claim 1, further comprising deriving a shape of a joint surface implant based, at least in part, on shape of subchondral bone derived from said image data.

46. The method according to claim 45, wherein said image data is three-dimensional image data.

47. The method according to claim 1, further comprising deriving a shape of a joint surface implant based, at least in part, on shape of cartilage derived from said image data.

48. The method according to claim 47, wherein said image data is three-dimensional image data.

49. The method of claim 15, wherein the bone cut is flat.

50. A method of making a surgical tool, the method comprising:
obtaining image data associated with at least a portion of a joint; and
deriving a substantially uncut cartilage surface associated with the joint from the image data; and
providing a surgical tool that includes a contact surface for engaging the substantially uncut cartilage surface associated with the joint, the surgical tool further including at least one guide for directing movement of a surgical instrument in preparing an implant site, wherein providing the surgical tool includes:
shaping the contact surface based on the derived cartilage surface such that the contact surface conforms to and is substantially a negative of the derived cartilage surface; and
determining position, shape and/or orientation of the at least one guide from the image data, so that changes induced on the implant site by the surgical instrument ensures a desired orientation of an implant wherein the shape of that at least one guide surface includes at least one of a groove, receptacle, and a notch, and wherein the shaped surface of the implant includes an extension that mates with the at least one of a groove, receptacle, and a notch so as to ensure a desired orientation of the implant.

51. A method of making a patient specific surgical tool for engaging a surface of a patella, the method comprising:
obtaining image data associated with at least a portion of the patella; and
deriving a substantially uncut cartilage surface associated with the patella from the image data; and
providing a surgical tool that includes a contact surface for engaging the substantially uncut cartilage surface associated with the patella, the surgical tool further including at least one guide for directing movement of a surgical instrument in preparing an implant site, wherein providing the surgical tool includes:
shaping the contact surface based on the derived cartilage surface such that the contact surface conforms to and is substantially a negative of the derived cartilage surface; and
determining position, shape and/or orientation of the at least one guide from the image data, so that changes induced on the implant site by the surgical instrument ensures a desired orientation of an implant.

52. The method according to claim 51, wherein providing the surgical tool includes providing a second component for engaging a first component, the first component including said contact surface.

53. The method according to claim 52, wherein said second component includes one or more of the at least one guide.

54. The method according to claim 52, wherein the surgical tool further includes an adjustment mechanism for adjusting the position and/or the orientation of at least one guide on the first and/or second component to a desired position relative to the contact surface to allow for ligament balancing.

55. The method according to claim 52, wherein the adjustment mechanism includes at least one of a spacer, a shim, a ratchet, a hinge, a tensiometer and a jack.

56. The method according to claim 52, wherein a surface of the first component that engages with a surface of the second component is configured to prevent at least one movement selected from the group consisting of axial, lateral and rotational.

57. The method according to claim 52, wherein a surface of the second component that engages the first component is at least one of convex or concave.

58. The method according to claim 52, wherein a surface of the first component that engages the second component is at least one of convex or concave.

59. The method according to claim 52, wherein a surface of one of the first component and the second component has an aperture for receiving at least one of a pin, post and peg located on a surface of the other of the first component and the second component.

60. The method according to claim 59, wherein the aperture forms a groove providing rotational movement.

61. The method of claim 51 further comprising:
engaging the contact surface of the surgical tool with the substantially uncut cartilage associated with the patella; and
directing movement of the surgical instrument in preparing an implant site using the at least one guide.

62. The method according to claim 51, wherein the at least one guide is one of a guide aperture, a reaming aperture, a drill aperture and a cut plane.

63. The method according to claim 51, wherein the shape of the at least one guide includes at least one guide element for ensuring the desired orientation of the implant.

64. The method according to claim 63, wherein the at least one guide element is a groove.

65. The method according to claim 51, wherein the guide has a keyed shape that corresponds to a keyed shape of the implant, such that changes induced on the implant site by the surgical instrument ensures that the implant interlocks with the implant site in the predetermined implant orientation.

66. The method according to claim 51, wherein the shape of the at least one guide directs the surgical instrument in making a bone cut that mates with a shaped surface on the implant to ensure the desired implant orientation.

67. The method according to claim 66, wherein the shaped guide surface is a groove, and the shaped surface of the implant is an extension.

68. The method according to claim 51, wherein obtaining the image data includes performing cross-sectional imaging.

69. The method according to claim 51, wherein obtaining the image data includes performing at least one of an MRI, a CT, an optical imaging modality, an x-ray imaging modality and an ultrasound.

70. The method according to claim 51, wherein obtaining the image data includes performing a spiral CT scan.

71. The method according to claim 51, wherein obtaining the image data includes scanning more than one joint.

72. The method according to claim 51, wherein determining shape and orientation of the at least one guide includes configuring a first guide to be at an angle to a second guide.

73. The method according to claim 51, wherein providing the surgical tool includes providing a stabilizer that engages the patella.

74. The method according to claim 73, wherein the stabilizer is selected from the group consisting of pin, peg, post, and nub.

75. The method according to claim 51, wherein providing the surgical tool includes further providing at least one of a spacer, a shim, a ratchet, a hinge, a tensiometer and a jack.

76. The method according to claim 51, further comprising determining, from said image data, the desired orientation of the implant in relation to at least one of an anatomic landmark, an anatomic axis, and a biomechanical axis associated with the patella.

77. The method according to claim 51, wherein the guide includes a metal covering.

78. The method according to claim 51, wherein the guide directs the surgical instrument in making a bone cut at a predetermined distance from a cartilage surface.

79. The method according to claim 51, wherein the surgical tool further includes an adjustment mechanism for adjusting the position and/or orientation of the at least one guide relative to the contact surface to allow for ligament balancing.

80. The tool according to claim 79, wherein the adjustment mechanism includes at least one of a spacer, a shim, a ratchet, a hinge, a tensiometer and a jack.

\* \* \* \* \*

UNITED STATES PATENT AND TRADEMARK OFFICE
CERTIFICATE OF CORRECTION

PATENT NO.       : 7,534,263 B2                                    Page 1 of 1
APPLICATION NO.  : 11/002573
DATED            : May 19, 2009
INVENTOR(S)      : Albert G. Burdulis, Jr. et al.

It is certified that error appears in the above-identified patent and that said Letters Patent is hereby corrected as shown below:

In Col. 24, line 24
replace "images"
with --image--

In Col. 24, line 59
replace "farther"
with --further--

In Col. 24, line 62
replace "tool"
with --method--

In Col. 28, line 29
replace "tool"
with --method--

Signed and Sealed this

Twenty-third Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.       : 7,534,263 B2                                        Page 1 of 1
APPLICATION NO.  : 11/002573
DATED            : May 19, 2009
INVENTOR(S)      : Albert G. Burdulis, Jr. et al.

It is certified that error appears in the above-identified patent and that said Letters Patent is hereby corrected as shown below:

In Col. 23, line 16
replace "images"
with --image--

Signed and Sealed this

Third Day of November, 2009

David J. Kappos
*Director of the United States Patent and Trademark Office*